US010682244B2

(12) United States Patent
McLean et al.

(10) Patent No.: US 10,682,244 B2
(45) Date of Patent: Jun. 16, 2020

(54) INSERTER FOR EXPANDING BODY TISSUE

(71) Applicant: SPINE WAVE, INC., Shelton, CT (US)

(72) Inventors: Scott McLean, Sandy Hook, CT (US); Nicola Cullinan, Bethel, CT (US); David Boisvert, Southington, CT (US)

(73) Assignee: SPINE WAVE, INC., Shelton, CT (US)

( * ) Notice: Subject to any disclaimer, the term of this patent is extended or adjusted under 35 U.S.C. 154(b) by 26 days.

(21) Appl. No.: 16/100,539

(22) Filed: Aug. 10, 2018

(65) Prior Publication Data
US 2018/0360623 A1 Dec. 20, 2018

Related U.S. Application Data

(63) Continuation of application No. 15/260,925, filed on Sep. 9, 2016, now Pat. No. 10,045,861, which is a
(Continued)

(51) Int. Cl.
A61F 2/46 (2006.01)
A61F 2/44 (2006.01)
A61F 2/30 (2006.01)

(52) U.S. Cl.
CPC ............ A61F 2/4611 (2013.01); A61F 2/447 (2013.01); A61F 2/4455 (2013.01); A61F 2/4603 (2013.01);
(Continued)

(58) Field of Classification Search
CPC .. A61F 2/4611; A61F 2002/4624–4629; A61F 2002/30579; A61F 2002/30599;
(Continued)

(56) References Cited

U.S. PATENT DOCUMENTS 3,486,505 A 12/1969 Morrison
4,524,766 A 6/1985 Petersen
(Continued)

FOREIGN PATENT DOCUMENTS

EP 0621020 A1 10/1994
FR 2639823 A1 6/1990
(Continued)

OTHER PUBLICATIONS

Baddeley, S. and Cullen, J.C., "The Use of Methylmethacrylate in the Treatment of Giant Cell Tumours of the Proximal Tibia", Aust. N.Z. J. Surg. vol. 49—No. 1, Feb. 1979, 3 pp.
(Continued)

Primary Examiner — Jacqueline T Johanas
(74) Attorney, Agent, or Firm — Hoffmann & Baron, LLP

(57) ABSTRACT

An elongate inserter has a distal end releasably connected to an expandable device for expanding body tissue and a proximal end including a trigger actuator. The expandable device comprises a superior endplate and an inferior endplate that are movable in an expansion direction relative to each other between opposing tissue surfaces of a body. The inserter includes a lifting platform comprising ramp surfaces that upon operation of the trigger actuator cooperatively engage complementary surfaces of expansion structure within the device to cause the superior and inferior endplates to move relatively away from each other. A driver is supported by the inserter for pushing an insert between the superior and inferior endplates after expansion of the device.

17 Claims, 23 Drawing Sheets

Related U.S. Application Data continuation of application No. 14/736,832, filed on Jun. 11, 2015, now Pat. No. 9,439,783, which is a continuation-in-part of application No. 14/474,639, filed on Sep. 2, 2014, now Pat. No. 9,114,026.

(60) Provisional application No. 61/948,660, filed on Mar. 6, 2014.

(52) U.S. Cl.
CPC . *A61F 2002/304* (2013.01); *A61F 2002/3008* (2013.01); *A61F 2002/30131* (2013.01); *A61F 2002/30484* (2013.01); *A61F 2002/30556* (2013.01); *A61F 2002/30579* (2013.01); *A61F 2002/30599* (2013.01); *A61F 2002/30601* (2013.01); *A61F 2002/30797* (2013.01); *A61F 2002/30904* (2013.01); *A61F 2002/4627* (2013.01); *A61F 2310/00017* (2013.01); *A61F 2310/00023* (2013.01); *A61F 2310/00239* (2013.01); *A61F 2310/00299* (2013.01); *A61F 2310/00317* (2013.01)

(58) Field of Classification Search
CPC ....... A61F 2002/30601; A61B 17/8802; A61B 17/8841
See application file for complete search history.

(56) References Cited

U.S. PATENT DOCUMENTS

| | | |
|---|---|---|
| 4,683,476 A | 7/1987 | Ferrari et al. |
| 4,736,738 A | 4/1988 | Lipovsek et al. |
| 4,743,493 A | 5/1988 | Sioshansi et al. |
| 4,755,797 A | 7/1988 | Kanaya |
| 4,863,476 A | 9/1989 | Shepperd |
| 4,888,024 A | 12/1989 | Powlan |
| 5,059,193 A | 10/1991 | Kuslich |
| 5,192,326 A | 3/1993 | Bao et al. |
| 5,192,327 A | 3/1993 | Brantigan |
| 5,197,971 A | 3/1993 | Bonutti |
| 5,298,254 A | 3/1994 | Prewett et al. |
| 5,431,658 A | 7/1995 | Moskovich |
| 5,439,684 A | 8/1995 | Prewett et al. |
| 5,505,732 A | 4/1996 | Michelson |
| 5,514,180 A | 5/1996 | Heggeness et al. |
| 5,522,899 A | 6/1996 | Michelson |
| 5,571,109 A | 11/1996 | Bertagnoli |
| 5,591,235 A | 1/1997 | Kuslich |
| 5,645,599 A | 7/1997 | Samani |
| 5,702,454 A | 12/1997 | Baumgartner |
| 5,755,797 A | 5/1998 | Baumgartner |
| 5,756,127 A | 5/1998 | Grisoni et al. |
| 5,766,252 A | 6/1998 | Henry et al. |
| 5,836,948 A | 11/1998 | Zucherman et al. |
| 5,860,977 A | 1/1999 | Zucherman et al. |
| 5,891,147 A | 4/1999 | Moskovitz et al. |
| 5,951,553 A | 9/1999 | Betz et al. |
| 5,980,522 A | 11/1999 | Koros et al. |
| 6,033,411 A | 3/2000 | Preissman |
| 6,045,579 A | 4/2000 | Hochshuler et al. |
| 6,066,154 A | 5/2000 | Reiley et al. |
| 6,074,390 A | 6/2000 | Zucherman et al. |
| 6,110,179 A | 8/2000 | Flivik et al. |
| 6,110,210 A | 8/2000 | Norton et al. |
| 6,159,211 A | 12/2000 | Boriani et al. |
| 6,159,244 A | 12/2000 | Suddaby |
| 6,183,517 B1 | 2/2001 | Suddaby |
| 6,190,414 B1 | 2/2001 | Young et al. |
| 6,200,347 B1 | 3/2001 | Anderson et al. |
| 6,241,771 B1 | 6/2001 | Gresser et al. |
| 6,273,916 B1 | 8/2001 | Murphy |
| 6,279,916 B1 | 8/2001 | Stecher |
| 6,287,308 B1 | 9/2001 | Betz et al. |
| 6,287,309 B1 | 9/2001 | Baccelli et al. |
| 6,290,724 B1 | 9/2001 | Marino |
| 6,387,130 B1 | 5/2002 | Stone et al. |
| 6,395,034 B1 | 5/2002 | Suddaby |
| 6,402,750 B1 | 6/2002 | Atkinson et al. |
| 6,419,705 B1 | 7/2002 | Erickson |
| 6,432,107 B1 | 8/2002 | Ferree |
| 6,436,142 B1 | 8/2002 | Paes et al. |
| 6,478,800 B1 | 11/2002 | Fraser et al. |
| 6,488,710 B2 | 12/2002 | Besselink |
| 6,500,205 B1 | 12/2002 | Michelson |
| 6,520,993 B2 | 2/2003 | James et al. |
| 6,562,074 B2 | 5/2003 | Gerbec et al. |
| 6,595,998 B2 | 7/2003 | Johnson et al. |
| 6,620,196 B1 | 9/2003 | Trieu |
| 6,648,917 B2 | 11/2003 | Gerbec et al. |
| 6,656,178 B1 | 12/2003 | Veldhuizen et al. |
| 6,726,691 B2 | 4/2004 | Osorio et al. |
| 6,740,093 B2 | 5/2004 | Hochschuler et al. |
| 6,837,904 B2 | 1/2005 | Ralph et al. |
| 6,852,095 B1 | 2/2005 | Ray |
| 6,852,126 B2 | 2/2005 | Ahlgren |
| 6,852,129 B2 | 2/2005 | Gerbec et al. |
| 6,863,673 B2 | 3/2005 | Gerbec et al. |
| 6,997,929 B2 | 2/2006 | Manzi et al. |
| 7,118,580 B1 | 10/2006 | Beyersdorff et al. |
| 7,329,283 B2 | 2/2008 | Estes et al. |
| 7,591,852 B2 | 9/2009 | Prosser |
| 7,722,625 B2 | 5/2010 | Sanders et al. |
| 7,905,921 B2 | 3/2011 | Kim et al. |
| 7,931,688 B2 | 4/2011 | Landry et al. |
| 7,967,867 B2 | 6/2011 | Barreiro et al. |
| 8,062,375 B2 | 11/2011 | Glerum et al. |
| 8,303,663 B2 | 11/2012 | Jimenez et al. |
| 8,303,879 B2 | 11/2012 | Bertele et al. |
| 8,308,805 B2 | 11/2012 | Lynn et al. |
| 8,337,562 B2 | 12/2012 | Landry et al. |
| 8,382,842 B2 | 2/2013 | Greenhalgh et al. |
| 8,585,761 B2 | 11/2013 | Theofilos |
| 8,628,578 B2 | 1/2014 | Miller et al. |
| 8,673,005 B1 * | 3/2014 | Pimenta ................ A61F 2/4455 623/17.11 |
| 8,715,351 B1 | 5/2014 | Pinto |
| 8,828,019 B1 | 9/2014 | Raymond et al. |
| 8,900,312 B2 | 12/2014 | McLean et al. |
| 9,114,026 B1 | 8/2015 | McLean et al. |
| 9,439,783 B2 | 9/2016 | McLean et al. |
| 10,070,970 B2 * | 9/2018 | Lynn ................ A61F 2/30744 |
| 2002/0026195 A1 | 2/2002 | Layne et al. |
| 2002/0147497 A1 | 10/2002 | Belef et al. |
| 2002/0177897 A1 | 11/2002 | Michelson |
| 2003/0171812 A1 | 9/2003 | Grunberg et al. |
| 2004/0019354 A1 | 1/2004 | Johnson et al. |
| 2004/0030387 A1 | 2/2004 | Landry et al. |
| 2004/0064144 A1 | 4/2004 | Johnson et al. |
| 2004/0220580 A1 | 11/2004 | Johnson et al. |
| 2005/0027364 A1 | 2/2005 | Kim et al. |
| 2005/0149194 A1 | 7/2005 | Ahlgren |
| 2005/0283244 A1 | 12/2005 | Gordon et al. |
| 2006/0058807 A1 | 3/2006 | Landry et al. |
| 2006/0058880 A1 | 3/2006 | Wysocki et al. |
| 2006/0129244 A1 | 6/2006 | Ensign |
| 2008/0119853 A1 | 5/2008 | Felt et al. |
| 2008/0154377 A1 | 6/2008 | Voellmicke |
| 2008/0161927 A1 | 7/2008 | Savage et al. |
| 2008/0172127 A1 | 7/2008 | Perez-Cruet et al. |
| 2008/0300598 A1 | 12/2008 | Barreiro et al. |
| 2009/0198339 A1 | 8/2009 | Kleiner et al. |
| 2009/0254182 A1 * | 10/2009 | Kovarik ................ A61F 2/447 623/17.11 |
| 2009/0306672 A1 | 12/2009 | Reindel et al. |
| 2010/0179594 A1 * | 7/2010 | Theofilos ................ A61F 2/44 606/247 |
| 2010/0312347 A1 | 12/2010 | Arramon et al. |
| 2011/0184522 A1 | 7/2011 | Melkent et al. |
| 2012/0022653 A1 | 1/2012 | Kirschman |
| 2012/0123548 A1 * | 5/2012 | Lynn ................ A61F 2/442 623/17.16 |
| 2012/0158144 A1 | 6/2012 | Ullrich, Jr. et al. |

(56) References Cited

U.S. PATENT DOCUMENTS

| | | |
|---|---|---|
| 2012/0191190 A1 | 7/2012 | Trieu |
| 2013/0090735 A1 | 4/2013 | Mermuys et al. |
| 2013/0103102 A1* | 4/2013 | Taylor .................. A61F 2/4611 606/86 A |
| 2013/0184825 A1 | 7/2013 | Kleiner |
| 2014/0277476 A1* | 9/2014 | McLean ................. A61F 2/442 623/17.16 |
| 2014/0364950 A1 | 12/2014 | Raymond et al. |
| 2015/0182346 A1* | 7/2015 | Emerick .............. A61F 2/4465 623/17.15 |
| 2015/0282943 A1* | 10/2015 | McLean ................. A61F 2/447 623/17.16 |
| 2015/0351923 A1* | 12/2015 | Emstad .............. A61F 2/30771 623/17.16 |
| 2018/0303631 A1* | 10/2018 | Phan ..................... A61B 17/70 |

FOREIGN PATENT DOCUMENTS

| | | |
|---|---|---|
| FR | 2719763 A1 | 11/1995 |
| WO | 9902214 A1 | 1/1999 |
| WO | 2013184946 A1 | 12/2013 |

OTHER PUBLICATIONS

Campanacci, M., Gui, L., Ranieri, L., Savini, R., "Treatment of Tibial Plateau Fractures", Chi. Org. Mov. 72(3), Dec. 1975 (Italian text), pp. 234-256, English Translation, 15 pp.

Kyphon Inc., Surgical Technique Manual Nov. 16, 1999, pp. 5, 6, 9, 16-19.

Kyphon web page, www.kyphon.com, Mar. 13, 2001, 1 p.

Signus Medical, TETRIS, Sep. 2003, 1 p.

Blackstone Medical Inc., Construx™ PEEK VBR System, 2005, www.blackstonemedical.com, 1 p.

\* cited by examiner

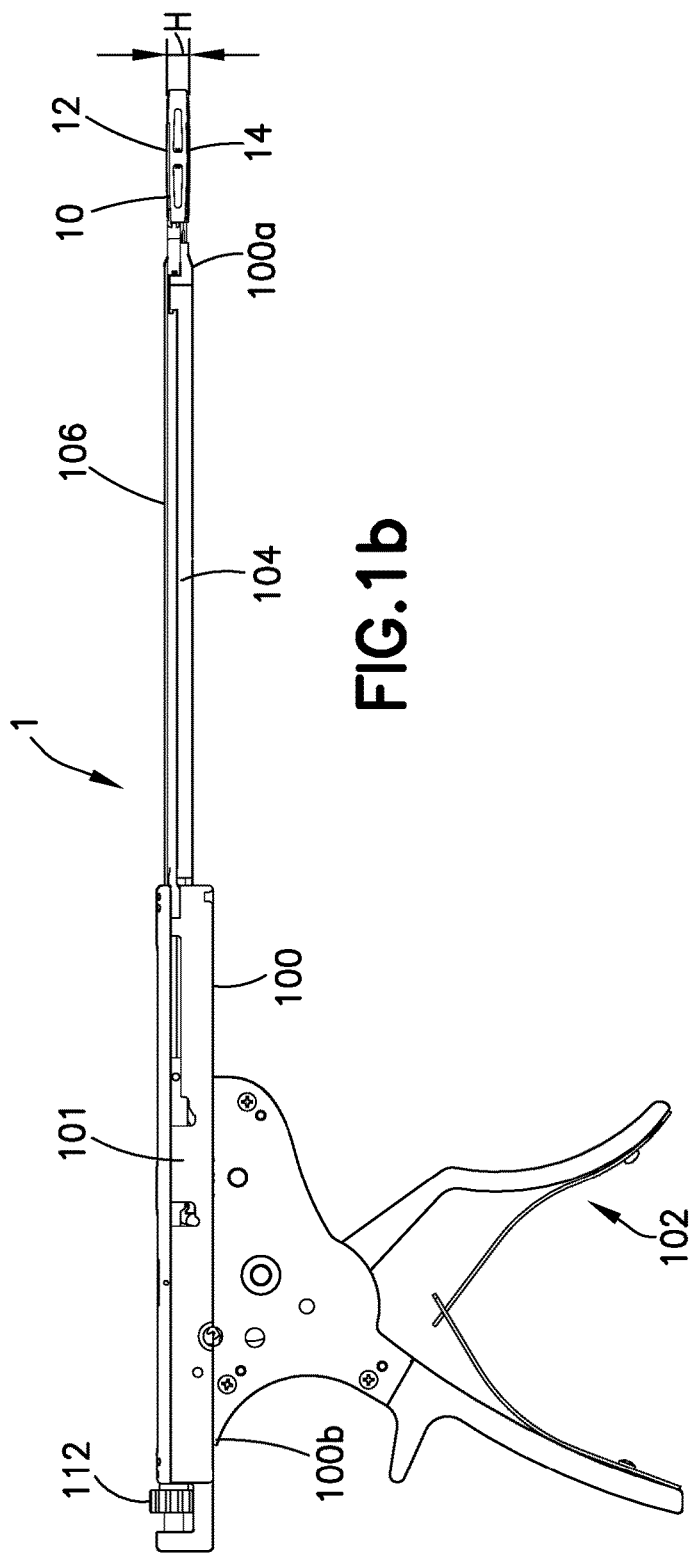
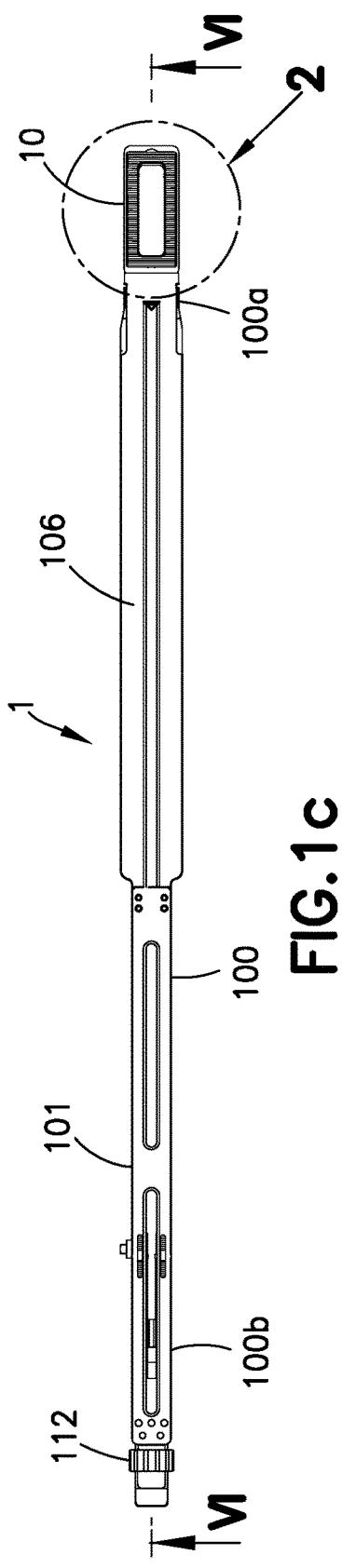

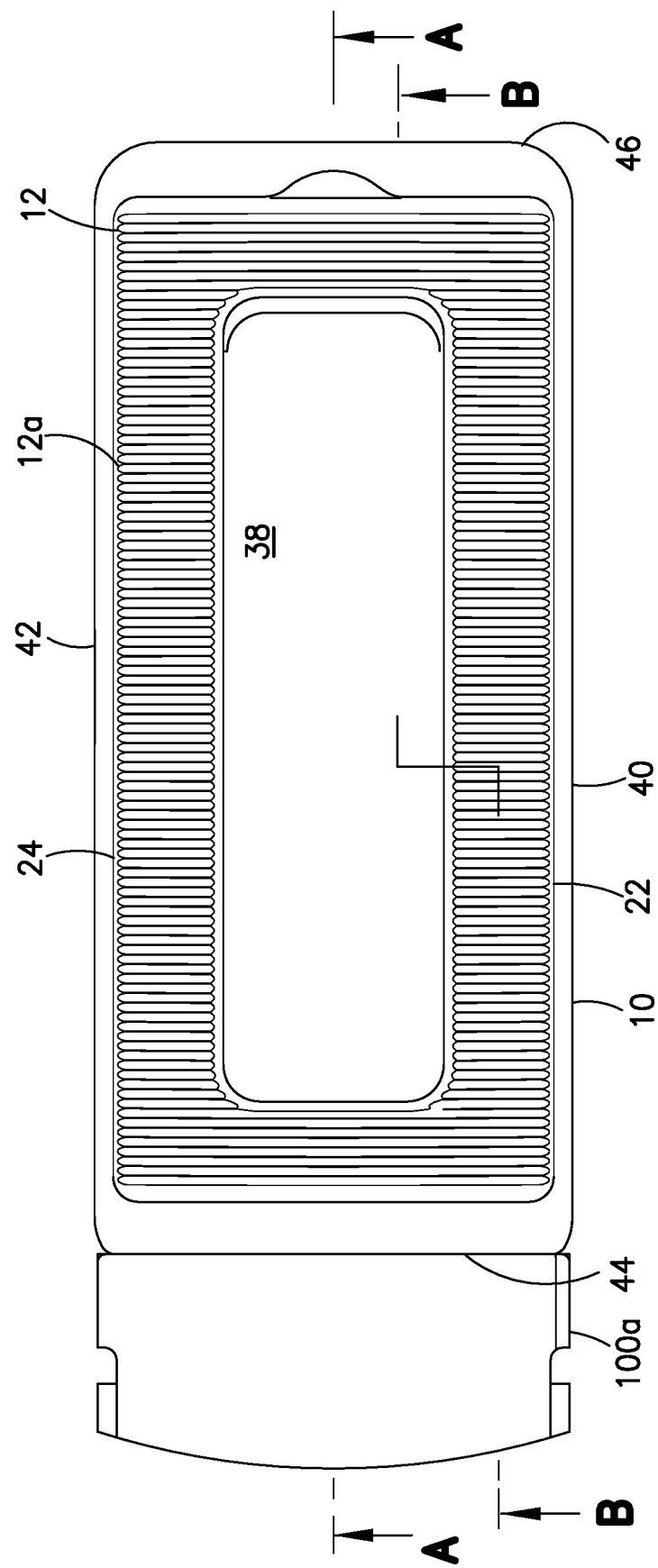

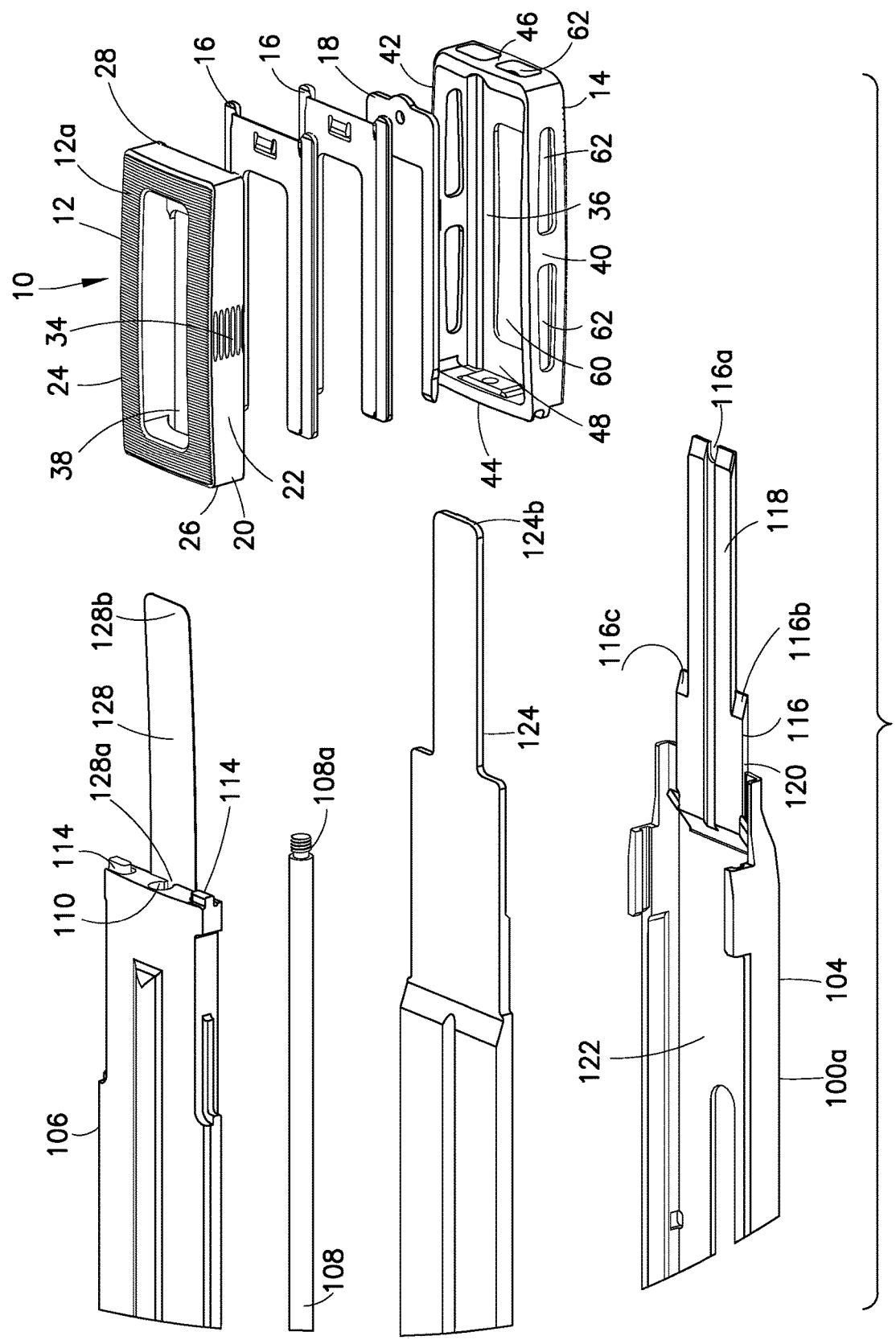

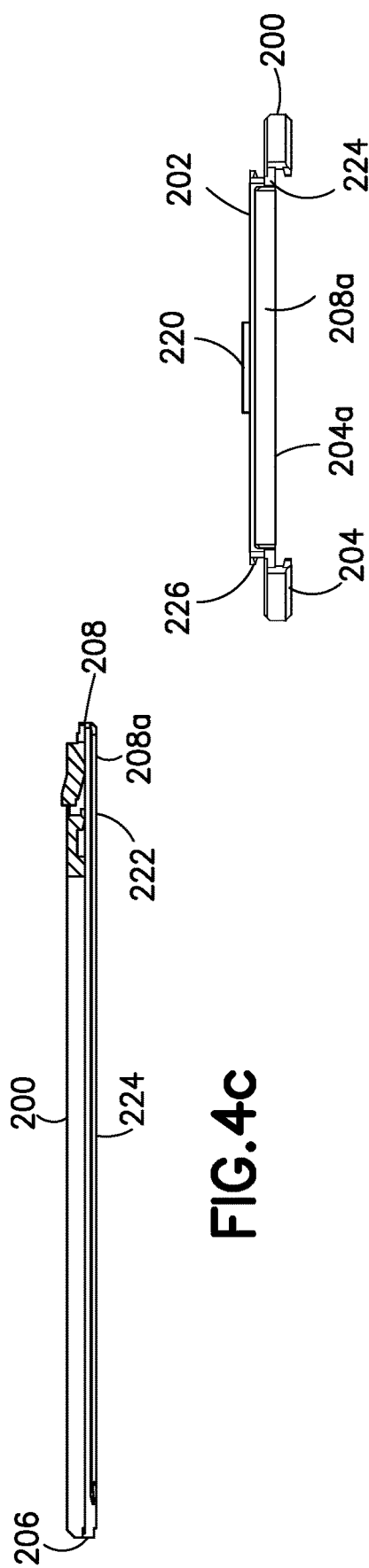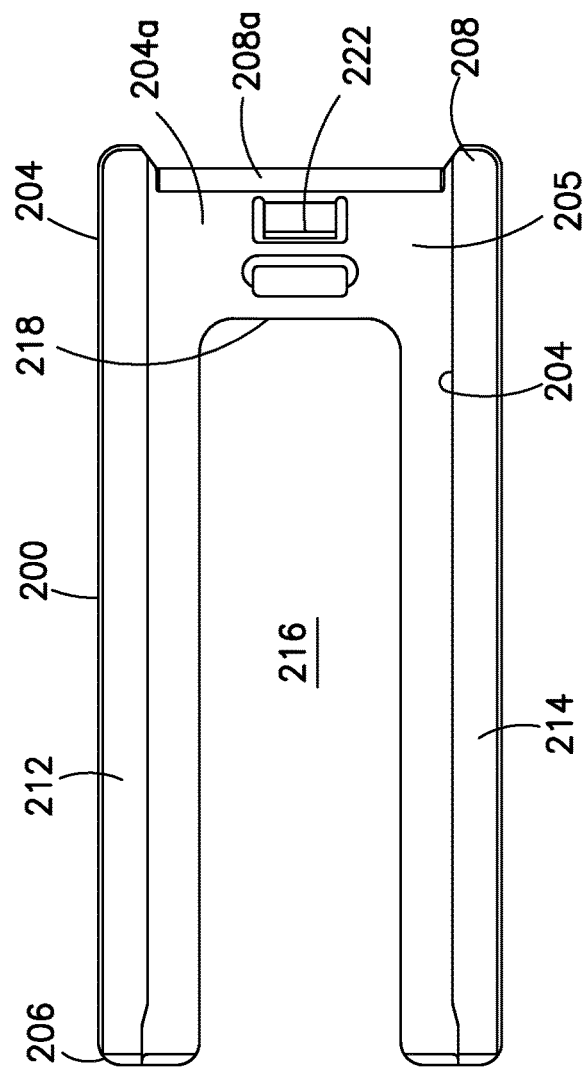

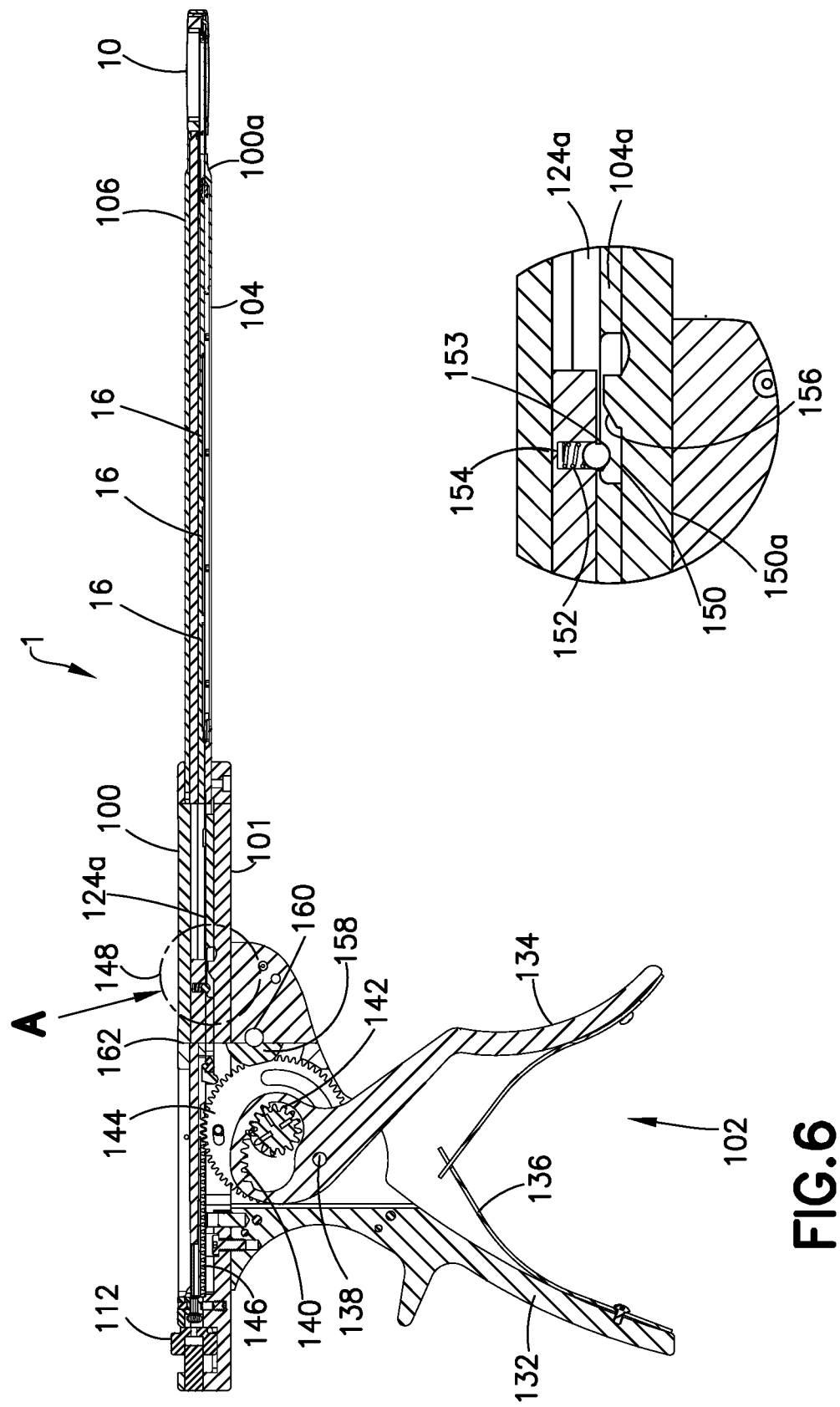

INSERTER FOR EXPANDING BODY TISSUE

CROSS-REFERENCES TO RELATED APPLICATIONS

This application is a continuation of U.S. application Ser. No. 15/260,925, filed Sep. 9, 2016, now U.S. Pat. No. 10,045,861, which is a continuation of U.S. application Ser. No. 14/736,832, filed Jun. 11, 2015, now U.S. Pat. No. 9,439,783, which is a continuation-in-part application of U.S. application Ser. No. 14/474,639, filed Sep. 2, 2014, now U.S. Pat. No. 9,114,026, which claims the benefit of U.S. Provisional Patent Application No. 61/948,660, filed Mar. 6, 2014, each of which is herein incorporated by reference in its entirety.

FIELD OF THE INVENTION

The subject invention relates generally to the field of surgery, and particularly to surgical devices, instruments and methods of using the same.

BACKGROUND OF THE INVENTION

A variety of physical conditions involves two bodily tissue surfaces that, for treatment of the condition, need to be separated from one another and supported away from one another. Such tissue expansion may be to gain exposure to select tissue structures, to apply a therapeutic pressure to select tissues, to return tissue structures to their anatomic position and form, or in some cases to deliver a drug or growth factor to alter, influence or deter further growth of select tissues. Depending on the condition being treated, the tissue surfaces may be opposed or contiguous and may be bone, skin, soft tissue, or a combination thereof.

One particular device for treating these conditions by distracting and supporting tissue surfaces simultaneously is described in U.S. Pat. No. 6,595,998, entitled "Tissue Distraction Device", which issued on Jul. 22, 2003 (the '998 Patent). Other examples of such tissue distracting and supporting devices that are used for achieving spinal interbody fusion are described in U.S. Pat. No. 7,931,688 entitled "Expandable Interbody Fusion Device", which issued on Apr. 26, 2011 (the '688 Patent), and U.S. Pat. No. 7,967,867 entitled "Expandable Interbody Fusion Device", which issued on Jun. 28, 2011 (the '867 Patent). The '998 Patent, the '688 Patent and the '867 Patent each discloses sequentially introducing in situ a series of elongate inserts referred to as wafers in a percutaneous approach to incrementally distract opposing vertebral bodies to stabilize the spine and correct spinal height, the wafers including features that allow adjacent wafers to interlock in multiple degrees of freedom. The '998 Patent, the '688 Patent and the '867 Patent are assigned to the same assignee as the present invention, the disclosures of these patents being incorporated herein by reference in their entirety.

An issue that has arisen regarding such interbody fusion devices that use inserts or wafers to incrementally expand such devices is the determination of when full expansion has been achieved as a result of ligamentotaxis and no further inserts may be inserted. It is therefore desirable for a surgeon to know when a sufficient number of inserts has been introduced to stabilize the spine and correct spinal height and whether any additional inserts may be introduced. One approach addressing this issue is described in commonly assigned U.S. Pat. No. 8,828,019, entitled "Inserter for Expanding an Expandable Interbody Fusion Device", issued on Sep. 9, 2014 ("the '019 Patent") and incorporated herein by reference in its entirety.

Accordingly, there is a need for an improved expandable interbody fusion device and inserter to expand and insert such a device, including the capability to determine when proper expansion of the device has been achieved and no further inserts may be introduced.

SUMMARY OF THE INVENTION

It is an object of the invention to provide an inserter for expanding an expandable device to expanding body tissue and for sequentially inserting one or more inserts after each incremental expansion of the device. A further object is the provision of the capability of the inserter to allow a surgeon to determine that suitable expansion has been reached and that no additional inserts may be inserted.

DESCRIPTION OF THE FIGURES

FIG. 1b is a side elevation view of the apparatus of FIG. 1a.

FIG. 1c is a top plan view of the apparatus of FIG. 1a.

FIG. 2 is an enlarged view of the distal portion of the apparatus as circled in FIG. 1c.

FIG. 3 is an exploded top perspective view of the distal end of the inserter and device of FIG. 1a.

FIG. 4a is a top perspective view of an insert used in the expandable spinal interbody fusion device of FIG. 1a.

FIG. 4b is a top plan view of the insert of FIG. 4a.

FIG. 4c is a longitudinal cross-sectional view of the insert as seen along viewing lines IV-IV of FIG. 4b.

FIG. 4d is a bottom plan view of the insert of FIG. 4a.

FIG. 4e is a distal end elevation view of the insert of FIG. 4a.

FIG. 5a is a top perspective view of an elevator used in the expandable spinal interbody fusion device of FIG. 1a.

FIG. 5b is a top plan view of the elevator of FIG. 5a.

FIG. 5d is a bottom plan view of the elevator of FIG. 5a.

FIG. 6 is a cross-sectional view of the inserter and device of FIG. 1a as seen along viewing lines VI-VI of FIG. 1c.

FIG. 6a is an enlarged view of the encircled portion A of FIG. 6.

DESCRIPTION OF THE EMBODIMENTS

Figure 1A:
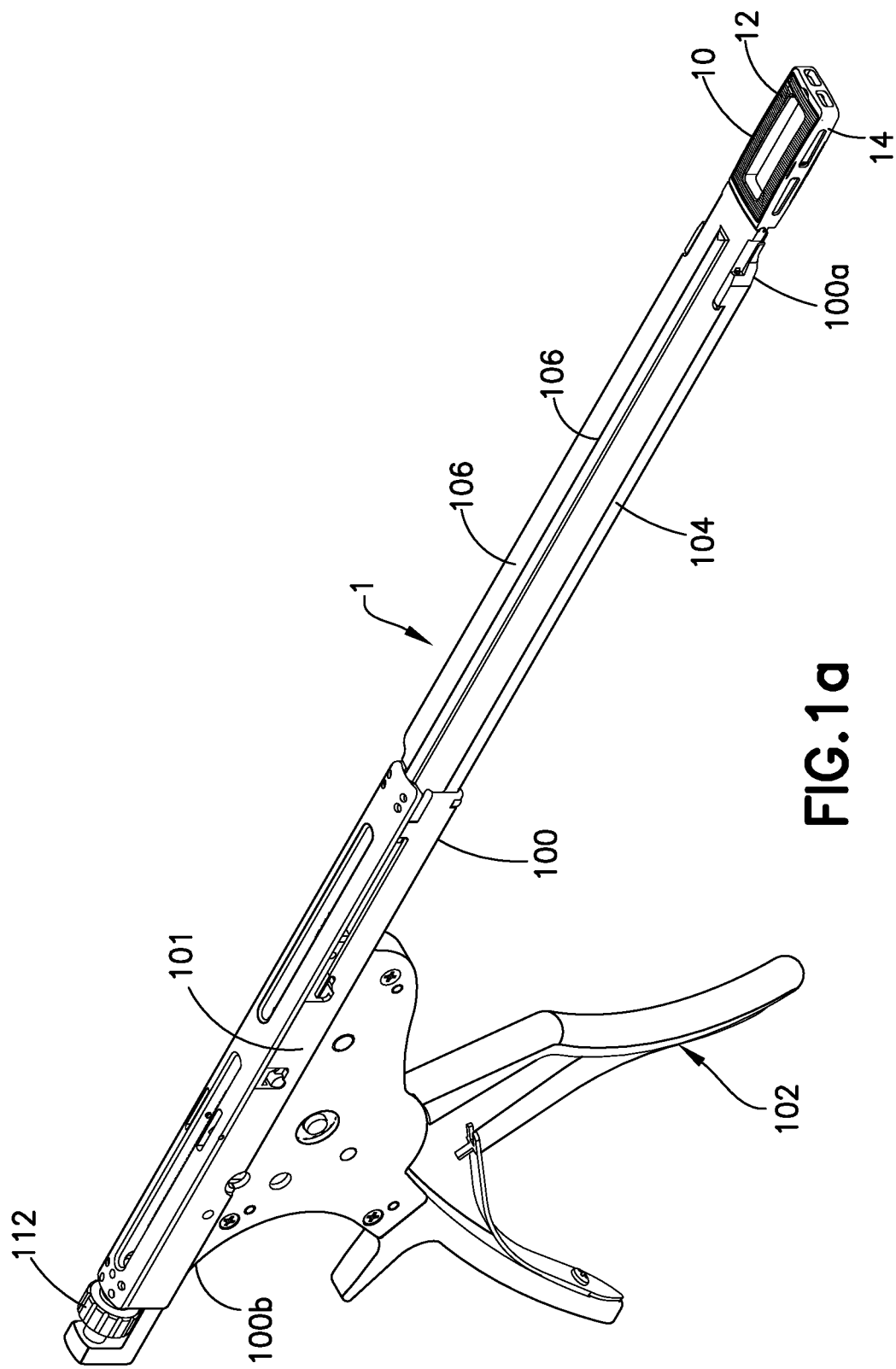
FIG. 1a is a top perspective of an apparatus including an inserter releasably attached to an expandable spinal interbody fusion device in accordance with an embodiment of the present invention, the expandable interbody fusion device being unexpanded.
Figure 4A:
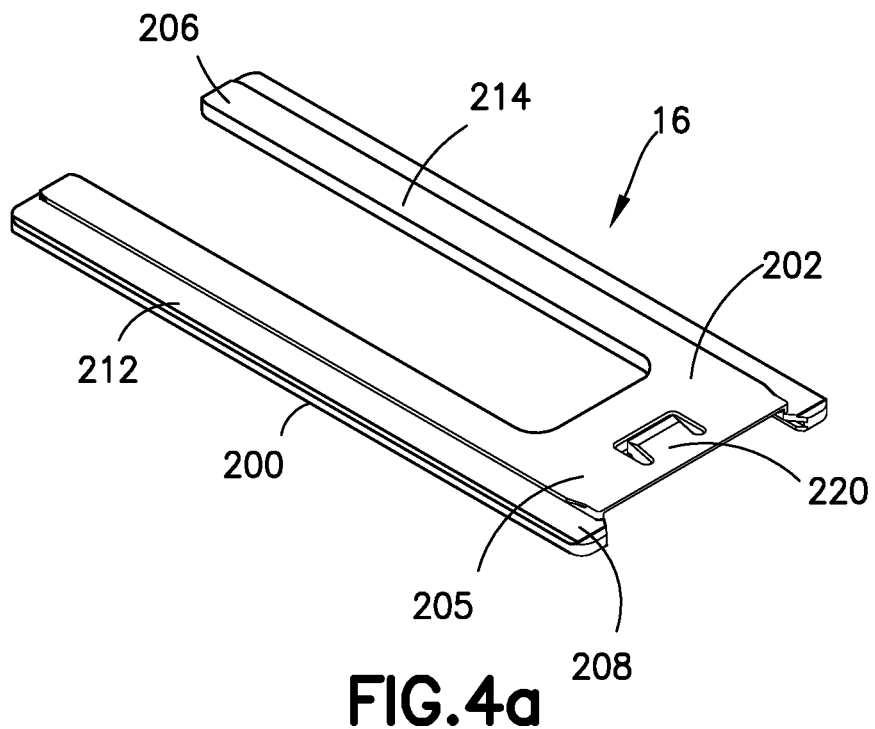
Figure 4B:
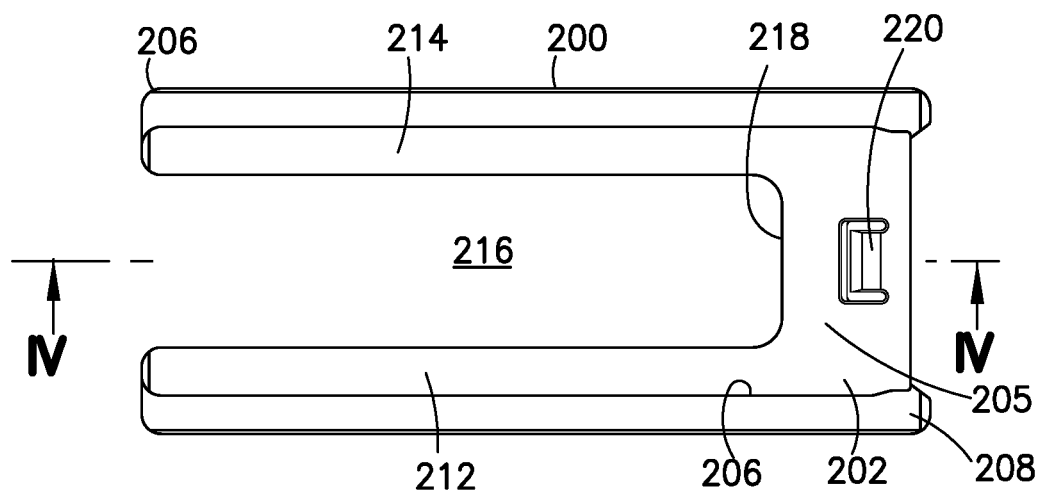
Figure 5A:
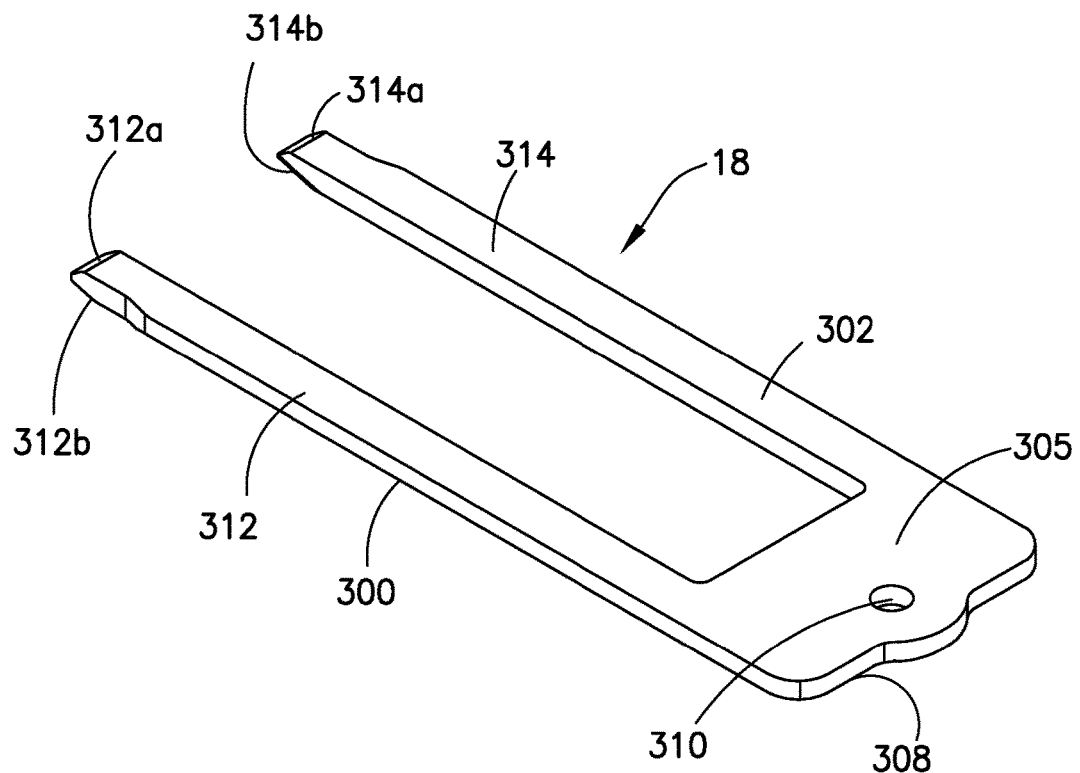
Figure 5B:
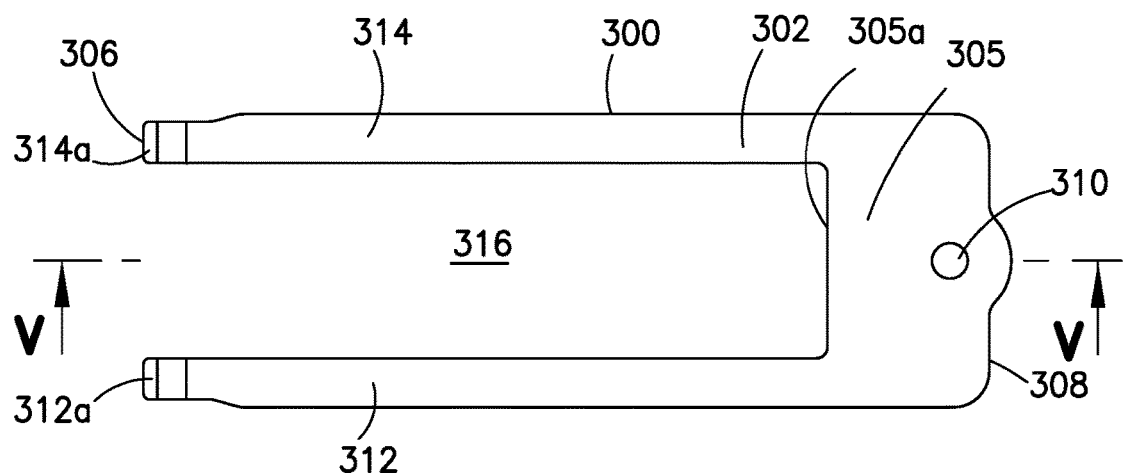
Figure 5C:
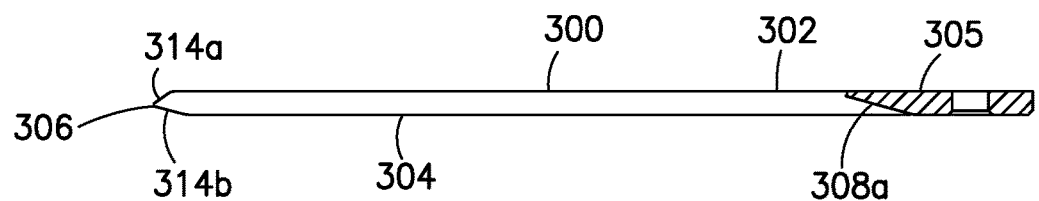
FIG. 5c is a longitudinal cross-sectional view of the elevator as seen along viewing lines V-V of FIG. 5b.
Figure 5D:
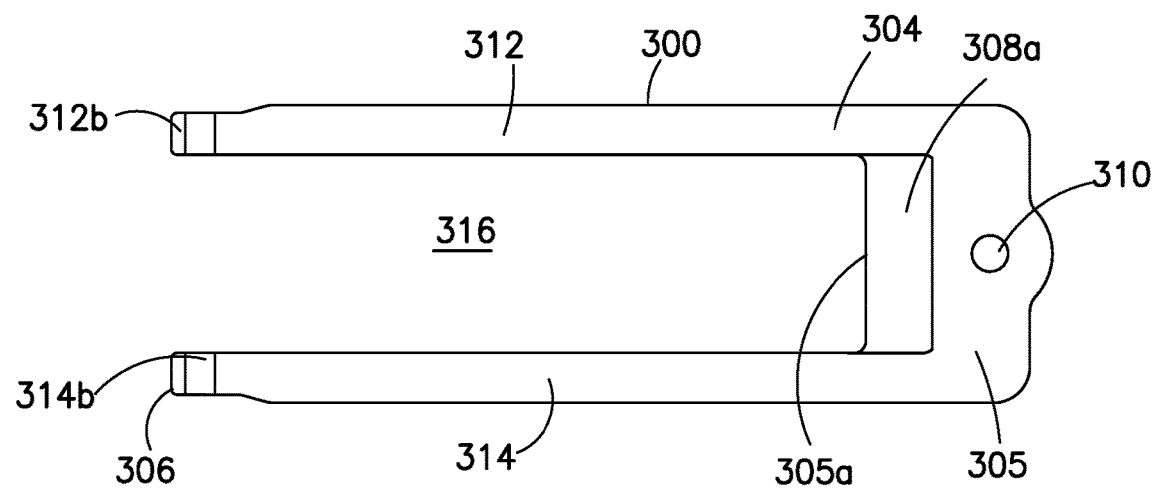

For the purposes of promoting and understanding of the principles of the invention, reference will now be made to the embodiments illustrated in the drawings and described in the following written specification. It is understood that no limitation to the scope of the invention is thereby intended. It is further understood that the present invention includes any alterations and modifications to the illustrated embodiments and includes further applications of the principles of the invention as would normally occur to one skilled in the art to which this invention pertains.

The invention provides a combination of an implantable expansion and support device and instrumentation to place the device into body tissue. The application of the invention as a spinal implant in spinal interbody fusion is detailed initially. Turning now to FIGS. 1a-c and FIGS. 2-3, an apparatus 1 for use in spinal interbody fusion is shown. Apparatus 1 comprises an expandable spinal interbody fusion device 10 and an inserter 100. The inserter 100 is an instrument used for inserting the device 10 into an intradiscal space between opposing vertebral bodies of a spine, expanding the device in situ and for inserting inserts into the expanded device 100. As shown in FIG. 3, the expandable interbody fusion device 10 includes a first element, such as superior endplate 12, a second element, such as inferior endplate 14, at least one insert 16 and expansion structure defined by an elevator 18, as will be detailed hereinbelow. The height, H, across the superior and inferior endplates 12, 14 in the unexpanded condition as illustrated in FIG. 1b is less than the normal anatomic height of a typical intradiscal space. The invention contemplates expanding the interbody fusion device 10 by the inserter 100 to ultimately restore the normal anatomic height of the disc space and thereafter inserting one or more inserts, such as interlocking inserts 16, as will be described, to form a stack of inserts 16 between the expanded superior endplate 12 and inferior endplate 14.

Figure 15:
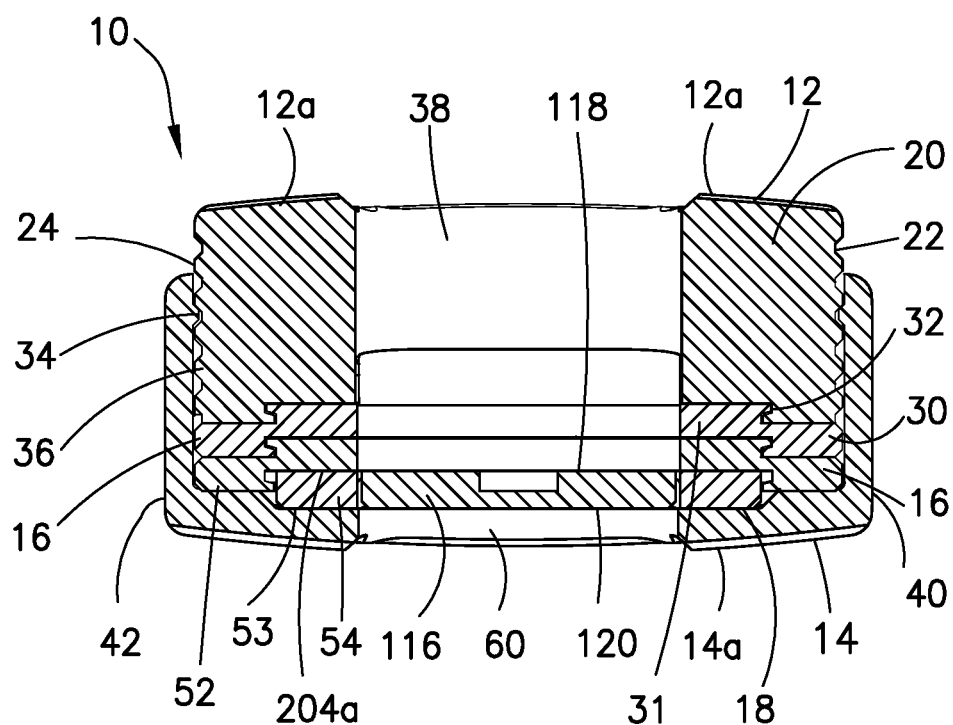
FIG. 15 is a cross-sectional view as seen along the viewing lines XV-XV of FIG. 14.

The superior endplate 12 as shown in FIGS. 3 and 15 is elongate and comprises a hub 20 having pair of side surfaces 22 and 24 extending longitudinally on each side of the hub 20 and a pair of end surfaces 26 and 28 extending respectively at the proximal rear end and the distal front end of the superior endplate 12. The hub 20 is sized and configured to fit within a cavity of the inferior endplate 14 for telescoping movement therewithin, as will be described. The lower surface 30 of the hub 20 (FIG. 15) includes a shaped configuration defined by a recessed interior surface 31 and insert interlocking features 32 that are substantially identical to the interlocking features on the lower surface of each insert 16, as will be described. The hub 20 defines a series of grooves 34 as shown in FIG. 3 extending along each side surface 22 and 24 thereof that are configured to engage ribs 36 projecting interiorly of the inferior endplate 14. This engagement temporarily holds the superior and inferior endplates together in the direction of expansion as the device 10 is introduced into the intradiscal space to be distracted.

As shown particularly in FIGS. 2-3 and 15, the superior endplate 12 includes a graft chamber defined by an opening 38 extending through the upper outer surface 12a and the lower interior surface 31. In accordance with one arrangement, the superior endplate 12 is formed of a biocompatible polymer such as polyethylethylketone (PEEK). PEEK is used in fusion applications for its combination of strength, biocompatibility, and elasticity which is similar to human bone. Other composites may include derivatives of PEEK such as carbon fiber reinforced PEEK and PEKK, respectively. In a particular aspect, the superior endplate 12 may further include an upper endcap that defines the outer surface 12a. The endcap may be a separate plate formed of material for the promotion of bone growth, such as titanium, and may be attached to the endplate 12 with suitable conventional techniques. As an alternative, the upper surface 12a may be defined by a coating of a suitable layer of bone growth promotion material, such as titanium, which may be deposited by conventional techniques.

The inferior endplate 14 of the interbody fusion device 10 as shown in FIGS. 2-3 and 15 is elongate and comprises a pair of opposing spaced apart sidewalls 40 and 42 extending along the longitudinal direction and projecting upwardly from the lower outer surface 14a. A pair of spaced apart end walls 44 and 46 extend laterally across the device and project upwardly from outer surface 14a. Rear end wall 44 is disposed at the rear or proximal end of the device 10 and front end wall 46 is disposed at the front or distal end of the device 10. The side walls 40, 42 together with rear end wall 44 and front end wall 46 form an open, upwardly facing fully bounded interior cavity 48 as shown in FIG. 3. The interior cavity 48 is sized and configured to receive the superior endplate 12 including the hub 20 in relatively close fit between the side walls 40 and 42 and the end walls 44 and 46 of the inferior endplate 14 in a non-expanded condition as shown in FIGS. 1a-b. The hub 20 of superior endplate 12, as well as the entire stack of inserts 16, remains fully contained within the inferior endplate 14 during telescoping expansion of the device 10 as shown in FIGS. 15 and 16, contributing to the torsional strength of the expanded device 10.

Figure 16:
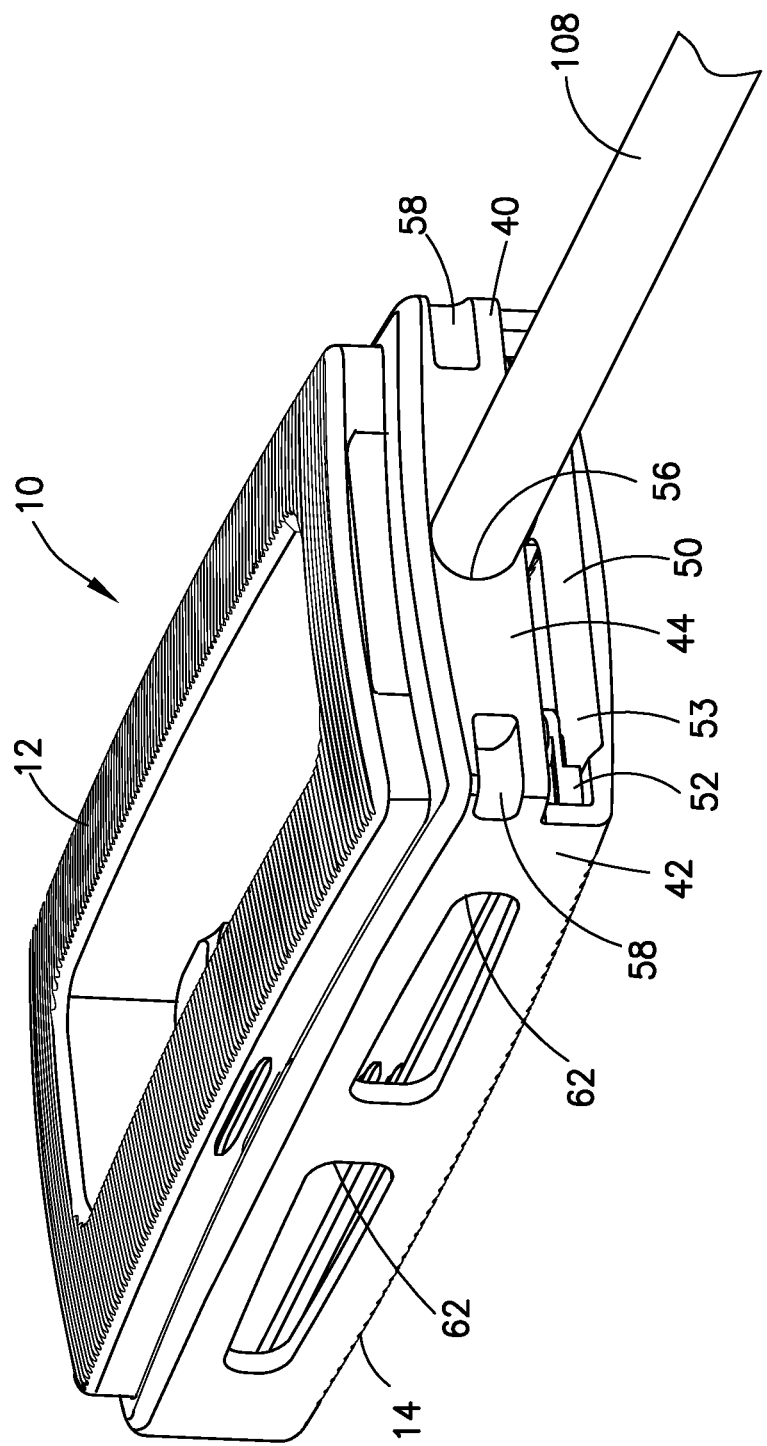
FIG. 16 is a proximal perspective view of the expanded spinal interbody fusion device with a guide pin releasably connected thereto subsequent to the inserter having been detached from the guide pin with inserts not being shown for clarity.

The inferior plate 14 as shown in FIG. 16 defines a fully bounded insert channel 50 extending through the rear end wall 44 in communication with interior cavity 48 and through which the inserts 16 are introduced. The inferior endplate 14 includes a pair of opposite ledges 52 that define a support surface on which each insert 16 is supported as it introduced into the insert channel 50, as will be described. The inferior endplate 14 further includes a lower inner support surface 54 on which the elevator 18 is supported. Lower inner surface 54 defines the bottom surface of the cavity 48 and a recess 53 bounded laterally by opposite ledges 52. Inserts are introduced sequentially into channel 50 on top of elevator 18, as will be described. The rear end wall 44 further defines a threaded connection opening 56 (FIG. 7a) for threaded releasable receipt of a guide pin for use in the introduction of inserts 16 and in the delivery of bone graft material into the device 10, as will also be described. Rear end wall 44 may also additionally include a pair of bilateral openings, such as notches 58, adjacent the sidewalls 40 and 42 for use in releasably attaching the inserter 100 to the device 10 for the establishment of a rigid connection to the device 10 for insertion into the intradiscal space.

As shown particularly in FIGS. 3 and 15, the inferior endplate 14 includes a graft chamber defined by an opening 60 extending through the lower outer surface 14a and the lower inner surface 54 in communication with cavity 48. In accordance with one arrangement, the inferior endplate 14 is formed of a material different from the material of the superior endplate 12. In this aspect, the inferior endplate 14 may be formed of a biocompatible metal, such as titanium, for its strength properties. Titanium is chosen for strength, biocompatibility, processing capability, and fluoroscopic imaging properties (radiolucency). Other alternative materials include cobalt chrome, stainless steel (both stronger than titanium but much less radiolucent), or biocompatible ceramics such as silicon nitride or zirconia, which are radiolucent. Titanium and silicon nitride have demonstrated good apposition to bone and superiority to PEEK. In this regard where inferior endplate 14 is formed of titanium, the lower outer surface 14a would provide for the promotion of bone growth. Lower outer surface 14a may also, however, be coated with a suitable layer of bone growth promotion material, such as titanium, and deposited in a conventional manner so as to match the roughness/porosity of the superior endplate outer surface 12a.

Where inferior endplate 14 is formed of titanium or other suitable metal that is radiopaque, windows 62 may be formed through sidewalls 40 and 42 and/or through front endwall 46 as shown in FIGS. 3 and 16 so as to allow visual observation of bony through growth by suitable imaging techniques, such as fluoroscopy. Further details of interbody fusion device 10 are described in commonly assigned U.S. Pat. No. 8,900,312, patent application Ser. No. 13/795,054 entitled "Expandable Interbody Fusion Device with Graft Chambers", filed on Mar. 12, 2013 ("the '312 Patent") and incorporated herein by reference in its entirety.

Details of the interlocking insert 16 are shown in FIGS. 4a-e. The insert 16 comprises an elongate and generally flat body 200 having an upper surface 202 and a lower surface 204, both of which are generally planar and substantially parallel so that the inserts 16 can form a stable stack within the interbody fusion device 10 upon expansion. Insert 16 includes a trailing rear proximal end 206 and a leading front distal end 208. The body 200 is formed to have a generally U-shaped, horseshoe configuration, with a pair of spaced opposing arms 212 and 214 projecting rearwardly from a base 205 and defining a rearwardly facing generally U-shaped opening 216 extending through the rear end 206 and through upper surface 202 and lower surface 204. A surface 218 between the upper surface 202 and the lower surface 204 at the base 205 of opening 216 defines a pushing surface for receipt of a driver of inserter 10, as will be described. The opening 216 at the rear end of each insert 200 is provided to allow bone graft material to flow into the device 10 through the insert openings 216 and into the openings 38 and 60 extending through the superior endplate 12 and the inferior endplate 14, respectively. The front distal end includes an inclined surface 208a extending upwardly from and communicating with lower surface 204.

The insert 16 includes several features for interlocking engagement to the hub 20 and to adjacent inserts 16 in a complementary cooperative interlocking mating interface. One particular feature includes a locking element defined by a resiliently deflectable prong 220 that projects outwardly above the upper surface 202 at the insert base 205 in the direction of expansion of device 10. A complementary locking surface 222 is defined in the lower surface 204 of the insert 200 for resilient engagement with the prong 220 of a subsequent insert 16 as each insert 16 is inserted into device 100 to form a stack. The lower surface 204 of each insert body 200 includes a shaped configuration defined by a recessed interior surface 204a and insert interlocking features defining a T-slot configuration 224 for mating with a T-bar configuration 226 on the upper surface 202 of a successive insert 16. While one locking element is shown, it should be appreciated that more than one locking element may be formed, the structure and function of the prongs 220 and locking surfaces 222 being more fully described in the '312 Patent. However, unlike the inserts described in the '321 Patent, the inserts 16 described herein do not function to assist in the separation of superior endplate 12 and inferior endplate 14 or any subsequent inserts 16 inserted into interbody fusion device 16, as that lifting function is provided by inserter 100 in conjunction with elevator 18. It is contemplated that the inserts 16 described herein be formed of a biocompatible material that is sufficiently rigid to form a solid stack as the successive inserts are inserted into the device. Thus, in one specific embodiment, the inserts are formed of PEEK or a carbon-fiber reinforced PEEK, or similar polymeric material.

Turning now to FIGS. 5a-d, details of the elevator 18 are shown. The elevator 18 comprises an elongate and generally flat body 300 having an upper surface 302 and a lower surface 304, both of which are generally planar and substantially parallel. The elevator 18 has a thickness between upper surface 302 and lower surface 304 that is slightly greater than the thickness of insert 16. As such, when as noted below the thickness of an insert 16 is, for example, 1.0 mm, the thickness of elevator 18 may be 1.03 mm. Elevator 18 includes a trailing rear proximal end 306 and a leading front distal end 308. The elevator body 300 is formed to have a generally U-shaped, horseshoe configuration similar to the configuration of insert 16. Elevator body 300 includes a pair of spaced opposing arms 312 and 314 projecting rearwardly from a base 305 and defining a rearwardly facing generally U-shaped opening 316 extending through the rear end 306 and through upper surface 302 and lower surface 304. Base 305 has a rearwardly facing surface 305a that communicates with opening 316. The opening 316 at the rear end of elevator 18 is provided to allow bone graft material introduced into the device 10 to flow through the insert openings 216 of inserts 16 and into the openings 38 and 60 extending through the superior endplate 12 and the inferior endplate 14, respectively. The rear proximal end 306 includes an inclined surface 312a and 314a, respectively at the free end of each arm 312 and 314 extending downwardly from and communicating with the upper surface 302. The rear proximal end 306 further includes an inclined lifting surface 312b and 314b, respectively at the free end of each arm 312 and 314 extending upwardly from and communicating with the lower surface 304. The front distal end 308 includes adjacent base surface 305a an inclined lifting surface 308a extending upwardly from and communicating with lower surface 304. The inclined lifting surfaces 312b, 314b and 308a are angled in the same direction with approximately equal angles. The lifting surfaces 312b, 314b and 308a define inclined ramps with multiple points of contact for cooperative contact with complementary surfaces of an expansion component on the inserter 100 for lifting elevator 18, as will be described. Inclined surface 308a is generally centrally located along the elongate axis of elevator, while surfaces 312b and 314b are spaced bilaterally. Thus, lifting surfaces 308a, 312b and 314b define three triangulated points of contact. Lastly, elevator has a hole 310 extending though the elevator base 305 and the upper surface 302 and the lower surface 304. Hole 305 is sized to receive a post on the inferior endplate 14, as will be described. In one specific embodiment, the elevator 18 is formed of titanium alloy, type 2, which may be anodized for lubricity. Other materials, such as PEEK, may also be used as the material for elevator 18.

Turning again now to FIGS. 1a-c and FIG. 3, details of the inserter 100 are described. Inserter 100 is elongate having a distal end 100a and at a proximal end 100b a frame 101. A trigger actuator 102 to effect expansion of device 10 and insertion of inserts 16 into device 10 after expansion is attached to frame 101 at the proximal end 100b of inserter. A plurality of inserts 16 are movably supported in a linear array on track 104 for individual successive insertion into device 10. Track 104 supports at least one insert 16 and may, for example, support an array of five inserts 16, although fewer or more inserts 16 may be supported as desired.

The distal end 100a is shown in exploded detail in FIG. 3. The inserter 100 includes an elongate lower track 104 and an upper track cover 106, the cover 106 being slidably joined to track 104. Lower track 104 is configured as an upwardly facing open channel and is movably supported by frame 101. Cover 106 is fixedly secured to frame 101. An elongate guide pin 108 is supported by frame 101 and within an opening 110 extending lengthwise through the cover 106. The distal end 108a of the guide pin 108 is threaded for releasable threaded engagement into opening 56 in the proximal rear end wall 44 of the inferior endplate 14. The proximal end of guide pin 108 is provided with a threaded knob 112 for compressing and releasably attaching the frame 101 and cover 106 and thereby the inserter 100 to the device 10. The track cover 106, in one arrangement, includes a pair of opposing tabs 114 that engage corresponding notches 58 in rear wall 44 of inferior endplate 14 to assist in rigidly securing the inserter 100 to the device 10. It should be appreciated that other securement structure may be used to releasably attach the inserter 100 to the device 10. Track 104, in one embodiment, is formed of stamped stainless steel and cover 106 is an extruded aluminum alloy. Stainless steel or strong reinforced plastic could also be used for cover 106.

The track 104 at the distal end 100a of the inserter 100 supports an expansion component defined by an axially translatable lifting platform 116 attached to track 104 for common axial movement therewith to cooperatively contact elevator 18 for expanding the device 10. The lifting platform 116 is elongate and generally flat having an upper surface 118 and a lower surface 120, both of which are generally planar and substantially parallel (FIG. 15). The lifting platform 116 has a thickness between upper surface 118 and lower surface 120 that is dimensioned to be the same as the thickness of elevator 18, i.e., slightly greater than the thickness of an insert 16. Track 104 and thereby lifting platform 116 are supported by the inserter 100 for reciprocating axial movement in projecting and retracting directions. Track 104 includes a lower surface 122 on which inserts 16 are movably supported in a linear array. The proximal end of the track 104 is coupled to the trigger actuator 102 to effect such projecting and retracting directions, as will be described.

Lifting platform projects axially outwardly from track 104 and includes at its free distal end an inclined lifting surface 116a extending downwardly from and communicating with upper surface 118. At a location spaced proximally of lifting surface 116a, lifting platform further includes a pair of laterally spaced inclined surfaces 116b and 116c. The inclined lifting surfaces 116a, 116b and 116c are angled in the same direction with angles approximately equal to the angles respectively of inclined lifting surfaces 312b, 314b and 308a of elevator body 300. Inclined surfaces 116a, 116b and 116c define inclined ramps with multiple complementary points of contact for cooperative contact with elevator 18. Inclined surface 116a is generally centrally located along the elongate axis of lifting platform 116, while surfaces 116b and 116c are spaced bilaterally. Thus, lifting surfaces 116a, 116b and 116c define three triangulated points of contact that are located and spaced to cooperatively contact lifting surfaces 308a, 312b, and 314b, respectively during movement of lifting platform 116 in the projecting direction. Lifting platform 116, particularly inclined surfaces 116a, 116b and 116c, may be coated or otherwise include a suitable lubricant to facilitate sliding contact with elevator 18 for expansion of device 10. Where lifting platform 116 is made of stainless steel, for example, such lubricant may include a molybdenum disulfide ($MoS_2$) material.

Still referring to FIG. 3, inserter 100 further supports at its distal end 100a a driver 124 for axial translational movement within track 104. The proximal end 124a (FIG. 6) of driver 124 is coupled to trigger actuator 102 to effect translational movement of the driver 124, as will be described. The distal end of driver 124 comprises a pushing surface 124b sized and configured to enter into the opening 216 of an insert body 200 to engage pushing surface 218 and push the insert 16 from track 104 into the device 10 upon axial distal movement of driver 124.

With further reference still to FIG. 3, inserter 100 comprises a flexible graft shield 128 projecting distally from track cover 106. Graft shield 128 is supported at one end 128a in a cantilevered manner with an opposite end 128b being unsupported and free to flex. Graft shield 128 is elongate and generally flat and is sized and configured to substantially block communication between the opening 38 through the superior endplate 12 and inserts 16 slidably inserted into device 10. As will be described, graft shield 128 is configured to extend into device 10 through channel 50 between the superior endplate 12 and the expansion structure adjacent the lower interior surface 31 of the superior endplate 12.

Turning now to FIGS. 6 and 6a, the details of the trigger actuator 102 of the inserter 100 and its function are described. Trigger actuator 102 comprises a pair of hand grips 132 and 134 biased apart by a leaf spring 136. Hand grip 132 is fixedly secured to frame 101 of inserter 100. Hand grip 134 is pivotally connected to frame 101 at pivot point 138 and is movable toward hand grip 132 against the bias of leaf spring 136 by manual pressure. Hand grip 134 has internal gear teeth 140 that interface with a small diameter gear 142 that is rigidly coupled to a large diameter gear 144. Large diameter gear 144 interfaces with a gear rack 146 rigidly coupled to the proximal end 124a of the driver 124. The gear mechanism is sized to provide the appropriate translation of driver 124 in the projecting direction as trigger actuator 102 is actuated. Driver 124 is releasably coupled to the proximal end 104a of track 104 via a ball clutch 148. Bilateral ball bearings 150 residing in blind holes 152 and 153 within the driver 124 and track 104 respectively are biased partially within the track 104 by compression springs 154. Blind holes 153 within track 104 have a partial opening in the floor thereby exposing approximately half of the lower hemisphere 150a of the balls 150. When the coupled driver 124 and track 104 have achieved sufficient axial translation in the projecting direction to expand the device 10, the exposed portions 150a of the balls 150 contact bilateral fixed ramps 156 ejecting them from the blind holes 152 within track 104 thereby decoupling the track 104 and driver 124. Continued trigger actuation advances the driver 124 independently distally of track 104. Frame 101and hand grips 132, 134 are all formed of stainless steel in a particular arrangement, although other materials, such as aluminum alloys and plastics may also be used.

For the purpose of returning the track 104 to its original position in the retracting direction a cam 158 and a return gear (not shown) rotatable about an axis 160 are provided. The return gear interfaces with the large diameter gear 144. The cam 158 is rigidly coupled to return gear and is positioned to contact a notch 162 in the track 104 after an insert 16 has been partially inserted into the device 10. Further trigger actuation returns the track 104 to its original position while further inserting the insert 16. When full trigger actuation is achieved, the driver 124 and hand grips 132/143 are returned under the bias of the leaf spring136, and the ball clutch 148 is re-engaged. A two way ratchet mechanism (not shown) prevents unwanted motion in the wrong direction. Thus, during a single stroke operation of trigger actuator 102, the elevator 18 is lifted by lifting platform 116 upon translational movement of track 104 and lifting platform 116 in the projecting direction, driver 124 pushes an insert 16 into the expanded device 10, track 104 and thereby lifting platform 116 are retracted in the retracting direction, and finally driver 124 is retracted from device 10. Such single stroke of operation is initiated when hand grips 132/134 are in the starting position of FIG. 6 and is completed when hand grips 132/134 are returned to the starting position under the bias of leaf spring 136.

Turning now to FIGS. 7a-b and 8-9 the assembly of the device 10 and the inserter 100 is described. The superior endplate 12 and the inferior endplate 14 are assembled in an unexpanded condition to the inserter 100 with the superior endplate 12 residing fully within cavity 48 of inferior endplate 14. In such condition superior endplate 12 and the inferior endplate 14 are provisionally held together in the direction of expansion by the engagement of ribs 36 and grooves 34, as described hereinabove. The inserter 100 is releasably attached to the device 10 upon threaded engagement of the guide pin 108 into threaded opening 56 in the proximal rear end wall 44 of the inferior endplate 14. Graft shield 128 extends into device 10 through channel 50 between the superior endplate 12 and the elevator 18 adjacent the lower interior surface 31 of the superior endplate 12. With the inserter 100 fixed to the device 10, track 104 with joined lifting platform 116 and driver 124 are axially translatable relative to the device 10 in the projecting and retracting directions. In this unexpanded condition, there are no inserts 16 in the device 10. Inserts 16 are supported on track 104.

The elevator 18 is supported on lower inner surface 54 within recess 53 of inferior endplate 14 with the lateral width of elevator 18 being closely dimensioned to the opposite ledges 52 (FIG. 15). As such, lateral movement in a direction transverse to the direction of expansion is substantially constrained. In addition, inferior endplate 14 includes a post 14b projecting upwardly from lower inner surface 54 toward superior endplate 12. Post 14b slidably projects through the hole 310 extending through the base 305 of elevator 18. Post 14b substantially constrains movement of elevator 18 in the axial direction while the clearance in hole 310 allows free movement of elevator 18 in the direction of expansion along post 14b as shown by the arrow 130 in FIG. 7a. As such, elevator 18 is captively supported within inferior endplate 14 and is independently movable along the direction of expansion toward and away from each of the superior endplate 12 and the inferior endplate 14. However, with the inserter 100 attached to the device 10, elevator 18 is fixed in the axial direction relative to axial movement of lifting platform 116.

Figure 7A:
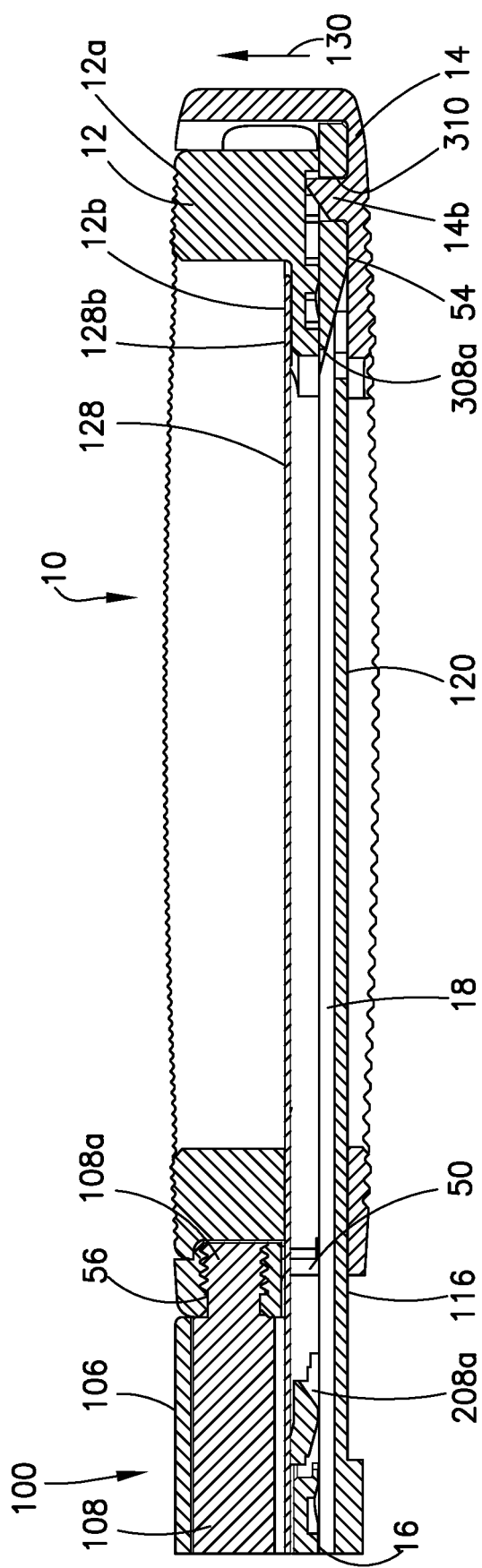
FIG. 7a is a cross-sectional view of the distal end of the inserter and device as seen along viewing lines A-A of FIG. 2 with the expandable device unexpanded.

In the position illustrated in FIGS. 7a-b and 8-9 lifting platform 116 is in a retracted position relative to device 10 and elevator 18. Insert 16, as seen in FIG. 7a, is disposed on track 104 exteriorly of and ready for insertion into device 10. In this position the lower surface 120 of lifting platform 116 is situated on lower inner surface 54 of inferior endplate 14. Likewise lower surface 304 of elevator 18 is supported by lower inner surface 54 of inferior endplate 14. As such, lifting platform 116 and elevator 18 are on substantially the same plane, with the upper surface 118 of lifting platform 116 being substantially coplanar with the upper surface 302 of elevator 18.

Figure 7B:
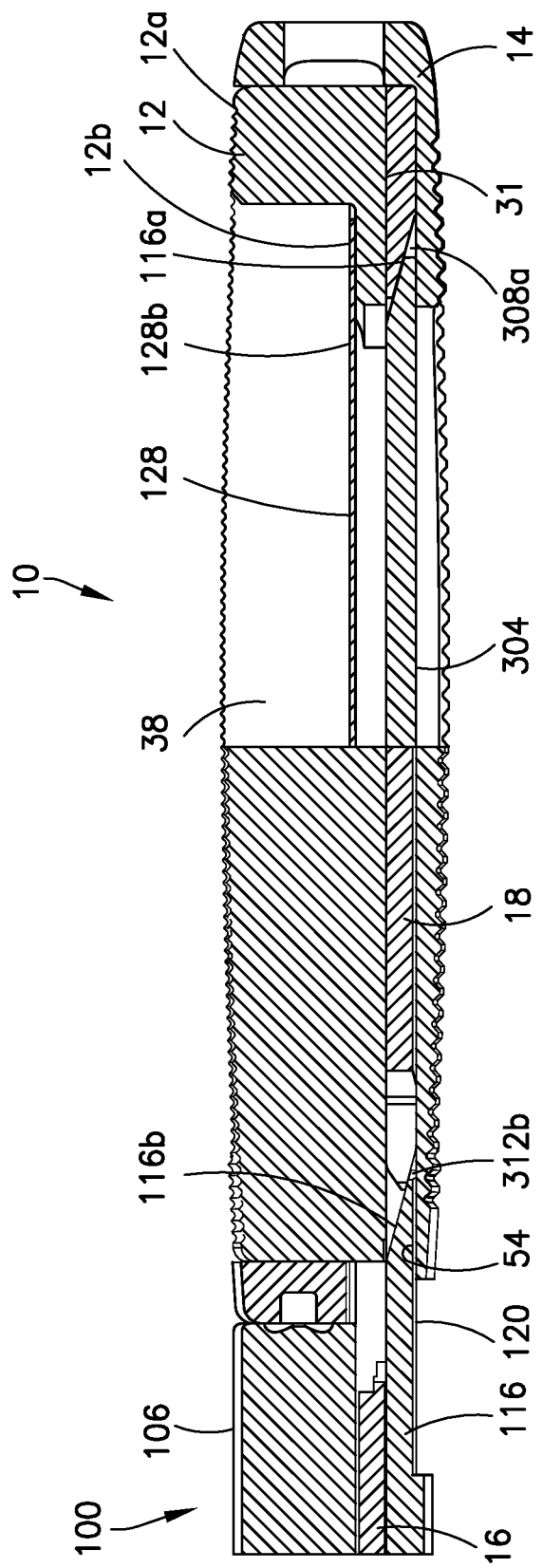
FIG. 7b is a cross-sectional view of the distal end of the inserter and device as seen along viewing lines B-B of FIG. 2 with the expandable device unexpanded.
Figure 8:
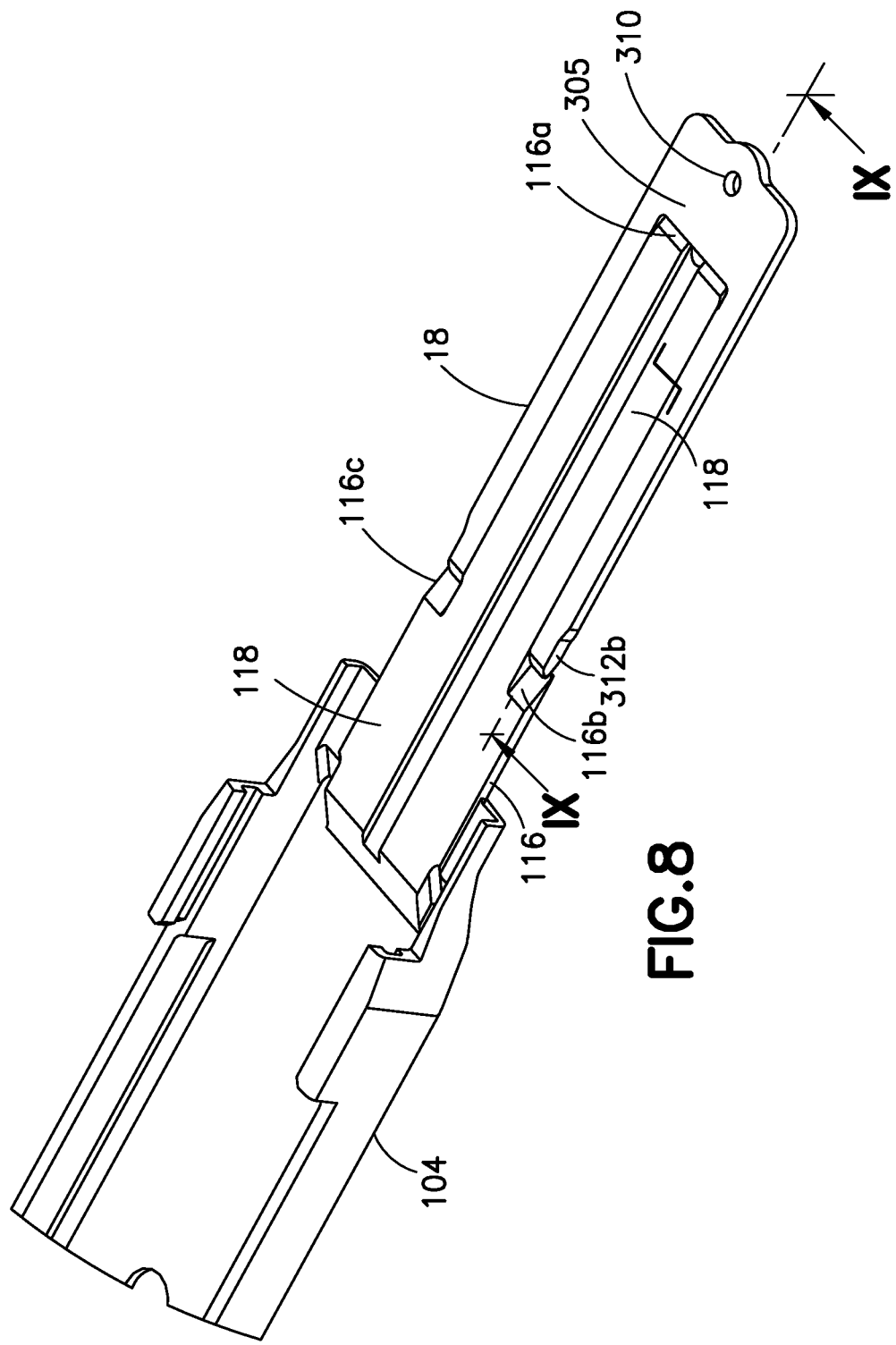
FIG. 8 is a top partial perspective view of the distal end of the lower track of the inserter showing a lifting platform and the elevator of the expandable device in the position depicted in FIGS. 7a and 7b.
Figure 9:
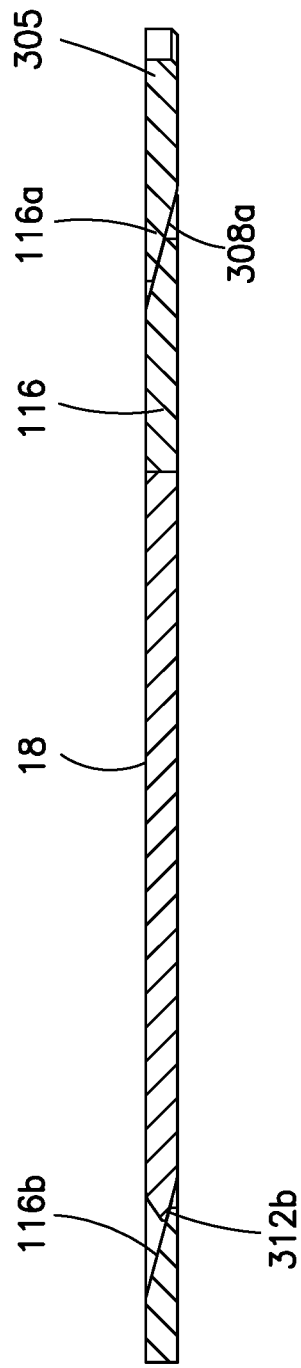
FIG. 9 is a cross-sectional view of the lifting platform and elevator as seen along viewing lines IX-IX of FIG. 8.

In the condition shown in FIGS. 7a-b, apparatus 1 comprising unexpanded device 10 releasably attached to inserter 100 is ready for use in inserting device 10 into an intradiscal space between two opposing vertebral bodies. Prior to insertion, opening 38 through superior endplate 12 may be pre-packed with a suitable bone graft material for the promotion of fusion through device 10 to the opposing vertebral bodies. Graft shield 128 extends into device 10 through channel 50 between the superior endplate 12 and the elevator adjacent the lower interior surface 31 of the superior endplate 12 defining a pocket for receipt of the graft material. The free end 128b of graft shield 128 rests unattached on an interior ledge 12b of superior endplate 12 adjacent the distal end thereof. Opening 38 is therefore open adjacent outer surface 12a of superior endplate 12 and closed by graft shield 128 adjacent lower interior surface 31. As such, graft shield 128 provides a barrier between the graft material and the elevator 18 and inserts 16 inserted into device 10 during expansion. Pre-packing of bone graft material in opening 38 on graft shield 128 advantageously allows for less introduction of graft material in situ and provides more assurance that sufficient graft material will be contained throughout device 10 and into openings 38 and 60 through superior endplate 12 and inferior endplates 14 and a stress-loaded condition against opposing vertebral bodies. In addition, graft shield 128 provides a barrier substantially preventing graft material within opening 38 from being disturbed during expansion and by substantially blocking graft material from interfering with the expansion of device 10 or with the slidable insertion of inserts 16 which may be impeded by graft material on the sliding interfacing surfaces.

Figure 10A:
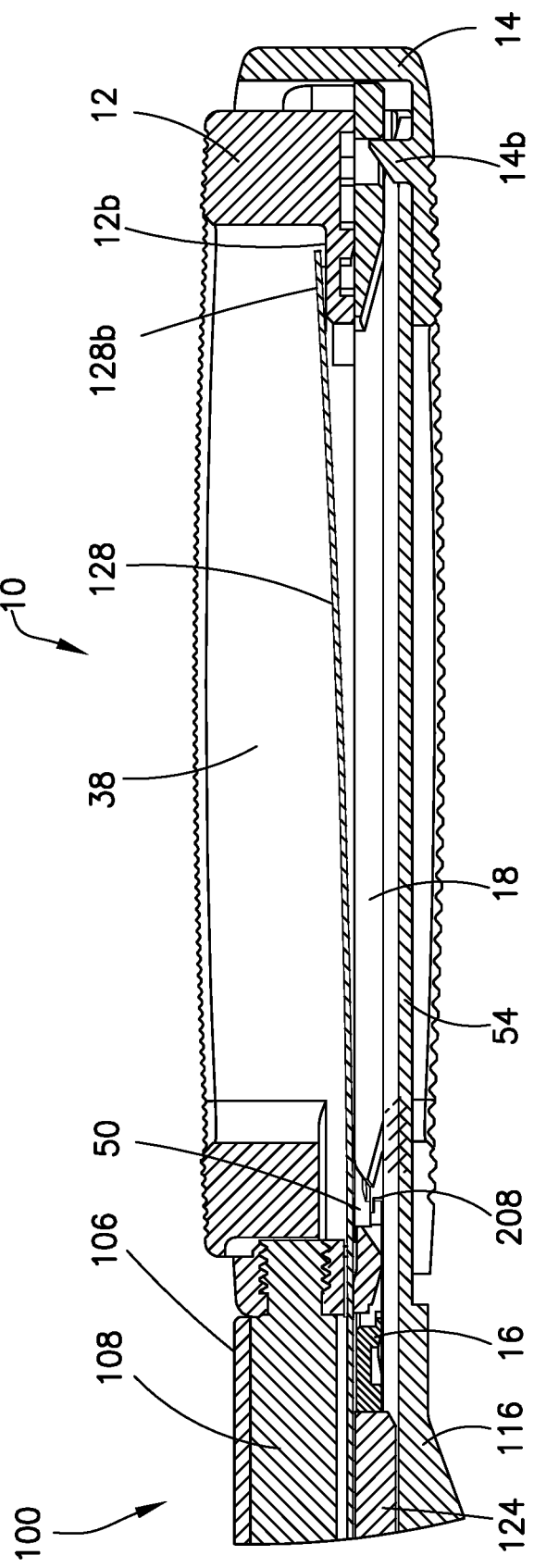
FIGS. 10a and 10b are views similar to FIGS. 7a and 7b with the lifting platform having been distally moved to a position lifting the elevator and expanding the expandable device and a first insert partially entering the expanded device.
Figure 10B:
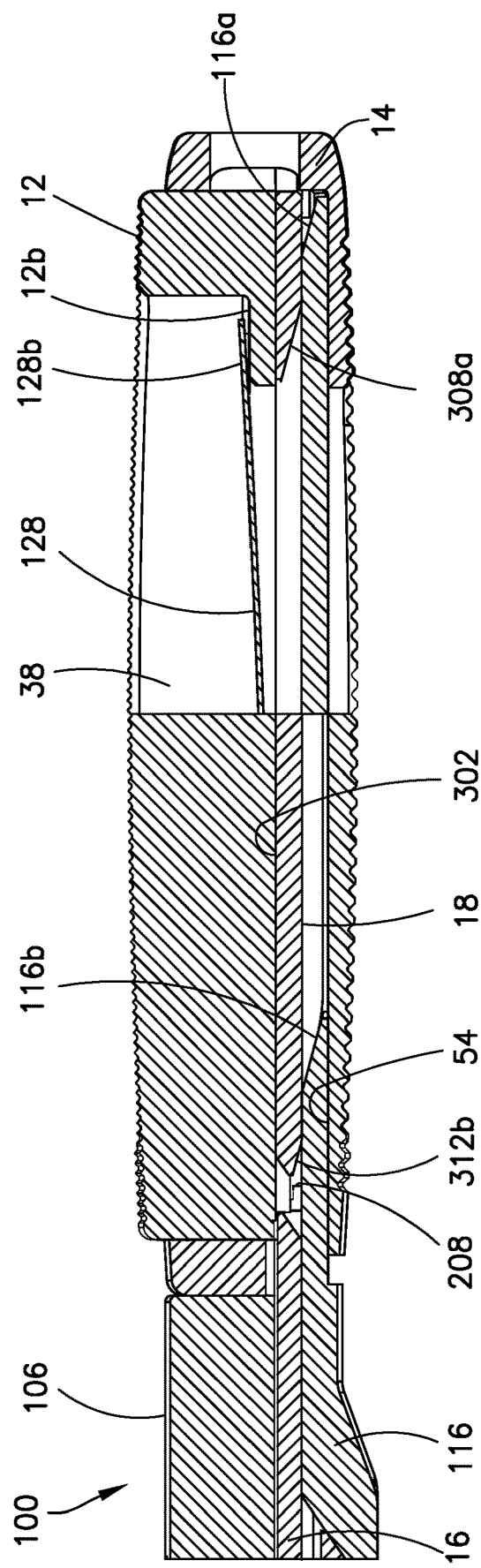

At this point in the surgical procedure, inserter 100 is used to insert unexpanded device 10 into the intradiscal space. Device 10 may be implanted into the spine posteriorly or posteriolaterally, either bilaterally or unilaterally, or in an anterior or lateral approach depending upon the surgical indication and the surgeons preference. Once device 10 is inserted in the intradiscal space in a suitable location, actuator 102 as described hereinabove is then operated. Initially during the stroke the track 104 with the attached lifting platform 116 and driver 124 are translated axially together. Lifting platform 116 is moved from the retracted position of FIGS. 7a-b to a projecting direction whereby lifting platform 116 is moved further into device 10. During movement in the projecting direction, lifting surfaces 116a, 116b and 116c of lifting platform 116 contact cooperative lifting surfaces 308a, 312b, and 314b, respectively of elevator 18. The cooperative engagement causes elevator 18 to move in the direction of expansion away from lower inner surface 54 of inferior endplate 14 and toward superior endplate 12. The upper surface 302 of elevator 18 contacts lower interior surface 31 of superior endplate 12 and elevator 18 slidably moves in the direction of expansion along post 14b toward superior endplate 12 and away from inferior endplate 14 as shown in FIGS. 10a-b, thereby expanding device 10. During this expansion, driver 124 continues to push insert 16 proximately toward device 10. Upon completion of expansion of device 10, the clutch 148 in the actuator 102 releases track 104 and thereby lifting platform 116 while movement of driver 124 continues in the distal direction. In this expanded condition, the distal front end 208 moves freely into expanded device 10 through channel 50 such that the distal front end 208 of insert 16 is partially inserted into expanded device 10 between superior endplate 12 and inferior endplate 14 adjacent the proximal end of device 10, as illustrated in FIGS. 10a-b.

Figure 11:
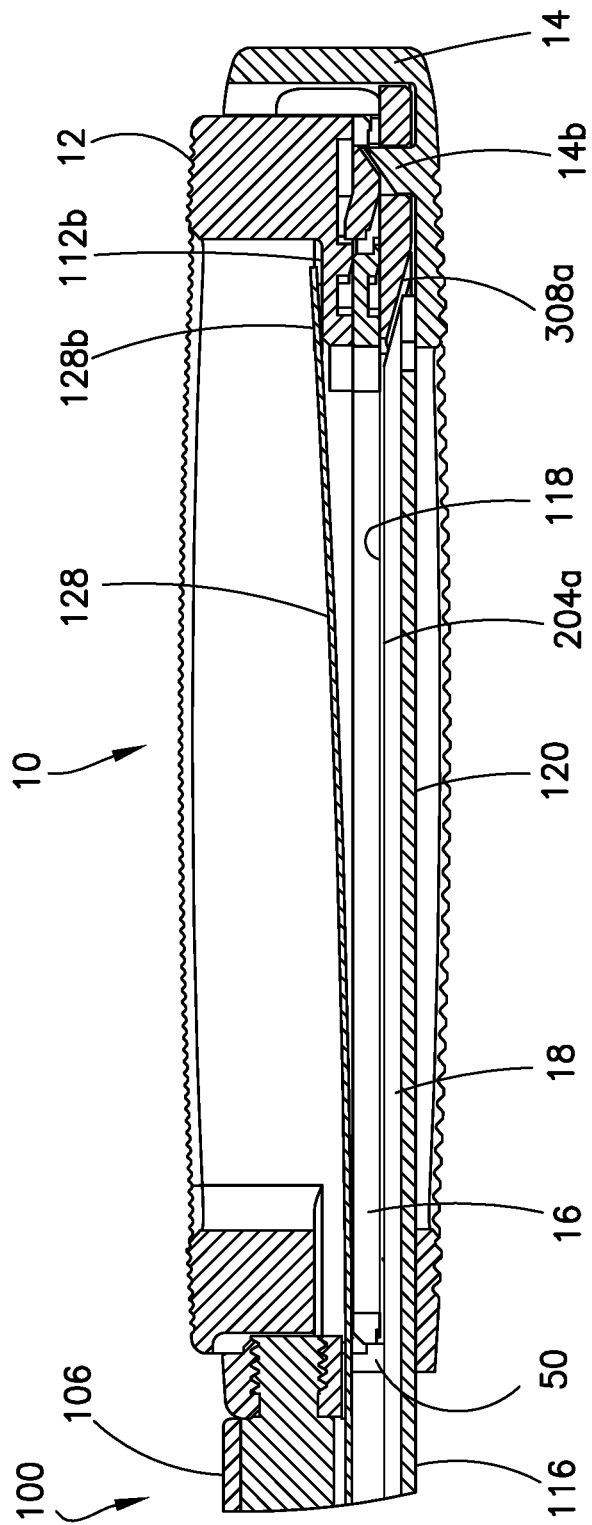
FIG. 11 is a view similar to FIG. 7a showing the first insert inserted into the expanded expandable device.

With insert 16 partially inserted in device 10, continued operation of the actuator 102 during the stroke causes cam 158 in the actuator 102 to pull track 104 with lifting platform 116 proximally thereby moving lifting platform 116 in a retracting direction. With distal front end 208 of insert 16 supporting superior endplate 12, continued proximal movement of lifting platform 116 causes lifting surfaces 116a, 116b and 116c of lifting platform 116 to sufficiently disengage cooperative lifting surfaces 308a, 312b, and 314b, respectively of elevator 18 to allow elevator 18 to move away in the direction of expansion from superior endplate 12 and toward inferior endplate 14 along post 14b and return to the position of elevator 18 shown in FIGS. 7a-b. As elevator 18 returns to the position whereby the lower surface 120 of lifting platform 116 is situated on lower inner surface 54 of inferior endplate 14, a space like space 64 described hereinbelow is created between lower interior surface 31 of superior endplate 12 and upper surface 302 of elevator 18. Such space is slightly greater than the thickness of an insert 16 and is in direct communication with lower interior surface 31 of superior endplate 12 and upper surface 302 of elevator 18. During completion of the stroke of actuator 102 driver 124 continues to move axially distally slidably pushing insert 16 fully into such space of expanded device 10, as shown in FIG. 11, with lower interior surface 204a of insert 16 facing and being in contact with upper surface 302 of elevator 18. Driver 124 is retracted proximally to the original position shown in FIGS. 7a-b when the hand grip 134 of actuator 102 is released and the clutch 148 is reengaged.

During insertion of insert 16 into device 10, the interlocking features described hereinabove on the upper surface 202 of insert 16 cooperatively interlock with the complementary interlocking features 32 on the lower surface 30 of superior endplate 12. Upon completion of insertion of insert 16, opening 216 of insert 16 is at least partially aligned with opening 38 of superior endplate 12 and opening 60 of inferior endplate 14. Once inserter 100 is removed from the expanded device upon completion of the surgical procedure, openings 216, 38 and 60 will all be in at least partial alignment and communication with each other.

Figure 12A:
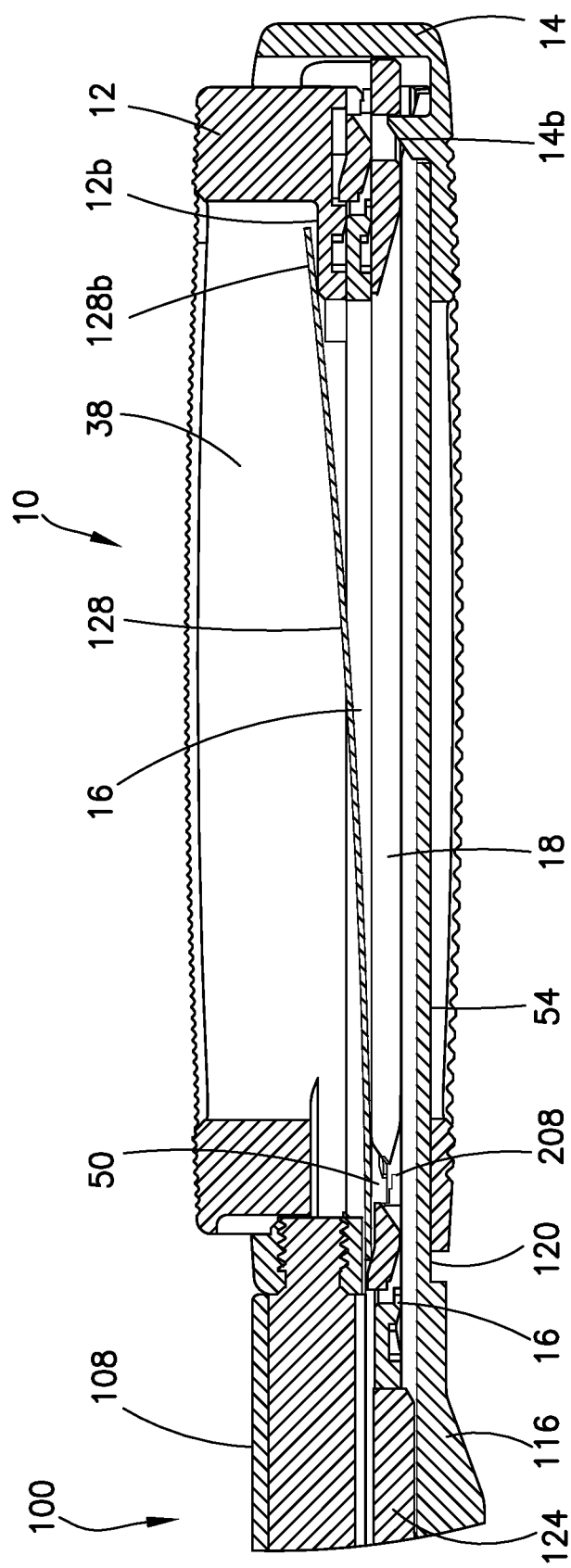
FIGS. 12a and 12b are views similar to FIGS. 10a and 10b with the lifting platform having been moved distally to a position lifting the elevator and the first insert to further expand the expandable device with a second insert partially entering the expanded device.
Figure 12B:
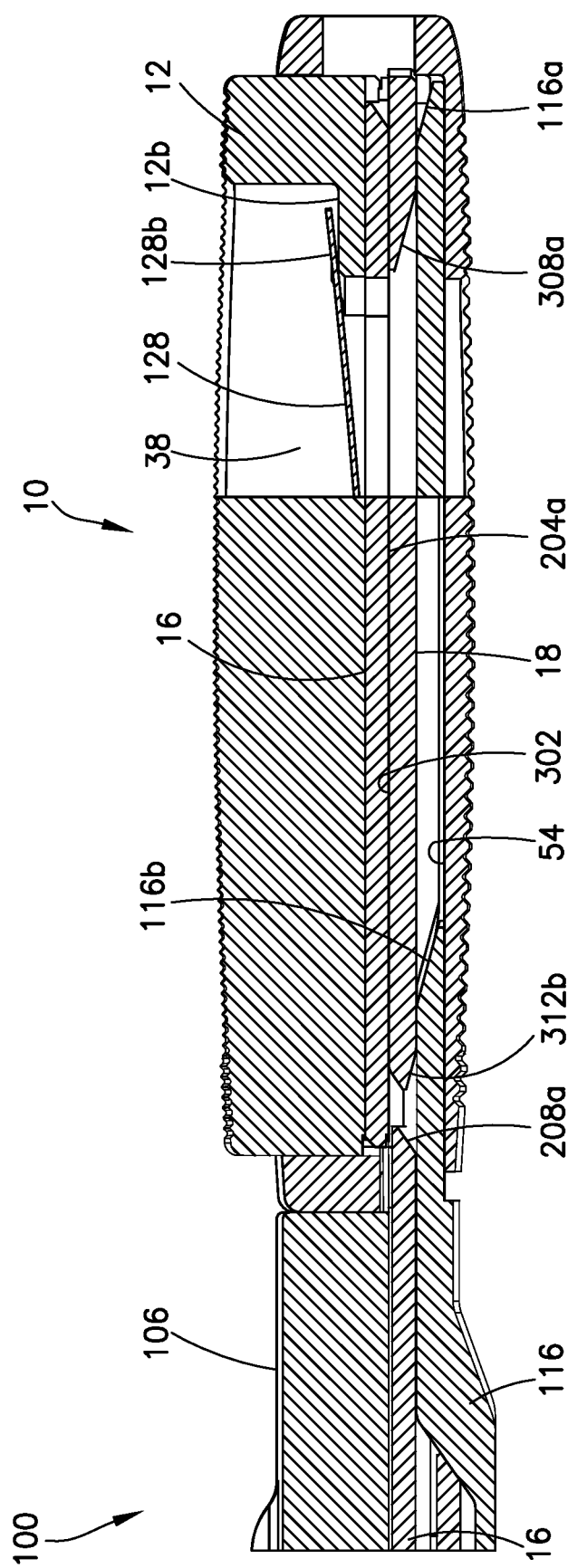
Figure 13A:
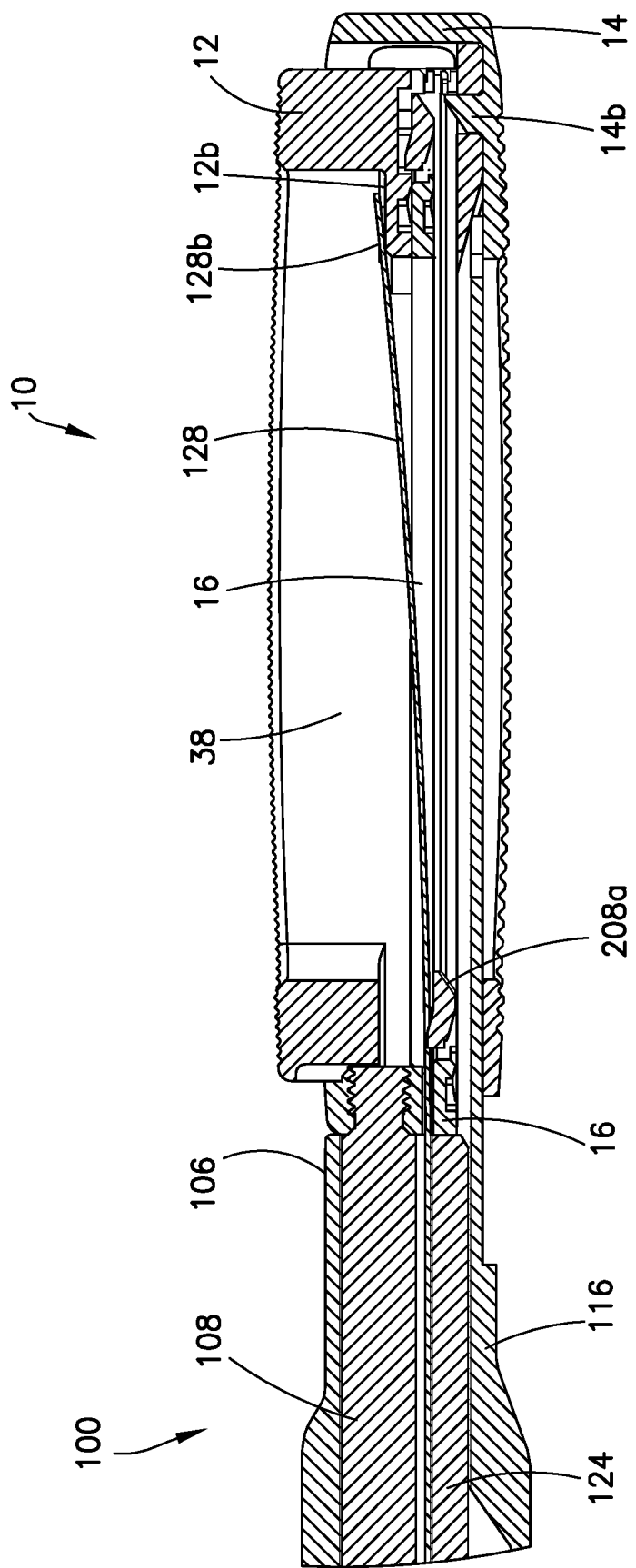
FIGS. 13a and 13b are views of the expandable device expanded as shown in the views of FIGS. 12a and 12b with the second insert having been further distally moved to a position moving the elevator away from the first insert and creating a space for the insertion of the second insert.
Figure 13B:
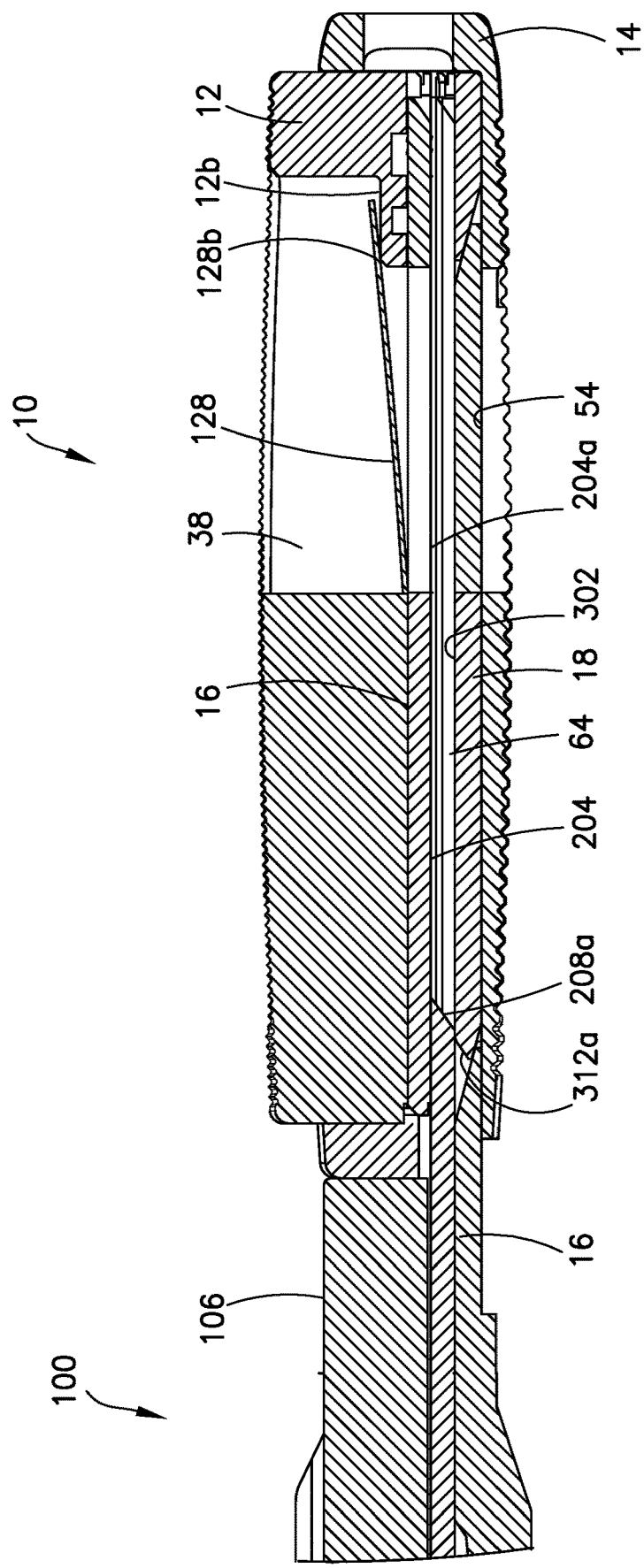

In the event the surgeon determines that additional inserts 16 are required in order to provide proper correction of the height of the intradiscal space, actuator 102 may be operated to insert one or more additional inserts 16 in the same manner as described with respect to the insertion of first insert 16. FIGS. 12a-b show device 10 with one insert 16 having been inserted and a second insert 16 partially introduced after device 10 has been further expanded by elevator 18 upon lifting by the lifting platform 116 in the same process as described with respect to FIGS. 10a-b. As the second insert 16 enters the further expanded device 10, the cam 158 in the actuator 102 as described above pulls lifting platform 116 proximally in a retracting direction, sufficiently disengaging lifting surfaces 116a, 116b and 116c of lifting platform 116 from cooperative lifting surfaces 308a, 312b, and 314b, respectively of elevator 18 to allow elevator 18 to freely return to inner surface 54 of inferior endplate 14. However, in the event elevator 18 fails to fully or partially return to such position, during continued pushing of second insert 16 into device 10 by driver 124, the inclined surface 208a at the front distal end 208 of second insert 16 contacts inclined surfaces 312a and 314a, respectively at the upper free end of each arm 312 and 314 of elevator 18, as shown in FIGS. 13a-b, to urge elevator 18 toward and against inner lower surface 54 of the inferior endplate 14 creating a space 64 between lower interior surface 204a of the first insert 16 and upper surface 302 of elevator 18. It should be understood that the feature urging elevator 18 toward inner lower surface 54 of inferior endplate 14 functions during the insertion of first insert 16 as well as all subsequently inserted inserts 16.

Figure 14:
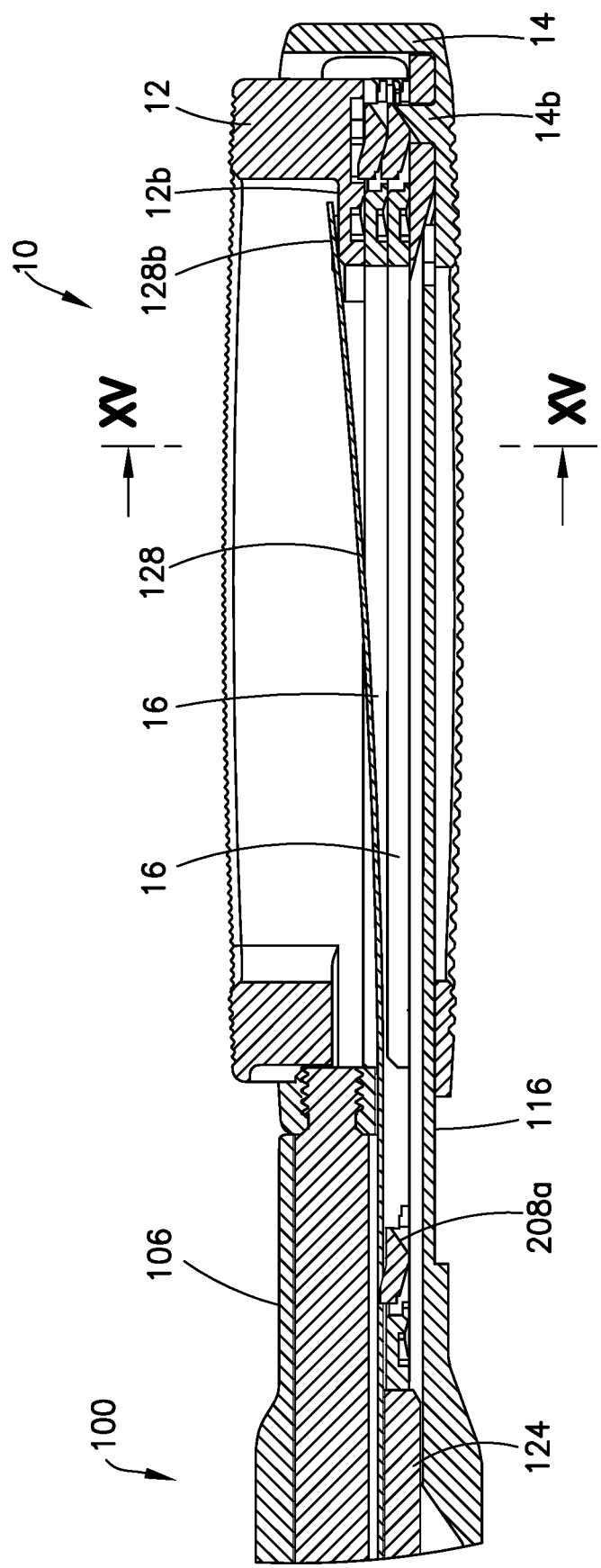
FIG. 14 is a view similar to the view of FIG. 11 showing the first and second inserts inserted into the expanded expandable device.

Continued operation of actuator 102 will continue to move second insert 16 until fully inserted shown in FIG. 14. During insertion of second insert 16 into device 10, the interlocking features described hereinabove on the upper surface 202 of the second insert 16 cooperatively interlock with the complementary interlocking features on the lower surface 204 of the first insert 16. Upon completion of insertion of second insert 16, opening 216 of insert 16 is at least partially aligned with opening 216 of the first insert, opening 38 of superior endplate 12 and opening 60 of inferior endplate 14, all of which will be in communication upon removal of inserter 100. The second insert 16 being the lowermost insert resides on and is supported on ledge 52 of inferior endplate 14 directly below and in interlocking contact with first insert 16. Driver 124 is then again retracted proximally to the original position shown n FIGS. 7a-b when the hand grip 134 of actuator 102 is released and the clutch 148 is reengaged in a position for insertion of a third insert 16, if required.

When the intradiscal space has been expanded to its maximum anatomic extent as the spine reaches ligamentotaxis and the device 10 cannot be further expanded, the surgeon will be able to determine such condition by tactile feedback. Completion of a stroke of actuator 102 and insertion is of an insert 16 into device 10 can only be achieved after elevator 18 reaches its ultimate movement in the direction of expansion toward superior endplate 12. As such, failure to compress hand grips 132/134 in a manner to complete the actuator stroke will allow the surgeon to recognize that ligamentotaxis has been reached and the proper intradiscal height has been restored. Inasmuch as the insertion of an insert 16 follows the expansion of device 10 upon full movement of elevator 18 in the direction of expansion toward inferior endplate 14, incomplete insertion of an insert 16 may be avoided. The surgeon would then terminate the procedure releasing hand grips 132/134, and then remove the inserter 100 from the expanded device 10 by rotatably removing knob 112 from the proximal end of guide pin 108. As shown in FIG. 16, the guide pin 108 may remain releasably connected to expanded device 10 to serve as a locator for subsequent attachment to an apparatus containing suitable bone graft to assist in the delivery of such material into a channel 50 of inferior endplate 14 through which inserts 16 were inserted.

In accordance with certain specific applications of device 10, the overall length of the device 10 as defined by the length of the inferior endplate 14, is about 45 mm. The width of the device 10 is approximately 19 mm. The height of the unexpanded device 10 of FIGS. 1*a-c* with the superior endplate 12 fully nested within the inferior endplate 14 is approximately 8 mm. With the introduction of five inserts 16, each of which has a thickness of approximately 1.0 mm, the height of device 10 may be expanded from an unexpanded height of approximately 8 mm to an expanded height of approximately 13 mm. Of course, the number of inserts 16 may vary depending upon the particular surgery and the initial height may also be different. For example, device 10 may be formed to have an initial unexpanded height of approximately 9 mm and with the addition of four inserts 16, each having a thickness of 1 mm, the height of device 10 may be increased to approximately 13 mm. As such, it should be appreciated that these dimensions are only illustrative and that the dimensions of the device 10 and the number of inserts to be inserted and their thicknesses may vary depending upon the application.

While the invention has been illustrated and described in detail in the drawings and foregoing description, the same should be considered as illustrative and not restrictive in character. It is understood that only the preferred embodiments have been presented and that all changes, modifications and further applications that come within the spirit of the invention are desired to be protected. For instance, an inserter with a graft shield, such as shield 128, may be used with expandable spinal interbody fusion devices having an expansion structure without an elevator 18 as described hereinabove. For example, an inserter with a graft shield 128 may be used with the expandable interbody fusion device shown and described in the '312 Patent referenced hereinabove wherein the device is expanded upon introduction of a series of wafers. Shield 128 may be used similarly as described herein to provide a barrier between a graft opening through one of the endplates, such as the superior endplate, and the wafers. Such a barrier would substantially prevent bone graft material pre-packed into such opening from interfering with sliding receipt of such wafers during insertion and expansion of the device. In addition, it should also be appreciated that actuators other than trigger actuators, such as with threaded rotary mechanisms, may be used with the inserter 100 described herein.

While one use of the invention as described herein is as an expandable spinal interbody fusion device, the invention may also be used in any situation where it is desirable to expand two tissue surfaces and to support such tissue surfaces after they have been separated. The tissue may be bone, skin, soft tissue, or combinations thereof. Further, the surfaces may be opposed surfaces of contiguous elements or surfaces of opposed elements. Thus, in addition to being used as a spinal interbody fusion device as set forth herein, the invention may also be used to treat vertebral compression fractures, for replacement of vertebral bodies (VBR), as a wedge opening high tibial osteotomy, tibial tuberosity elevation, as well as for treating other compression fractures including, but not limited to tibia plateau fractures, calcaneous, distal tibial fractures, or distal radius (wrist) fractures. One method for treating these conditions includes distracting and supporting the tissue surfaces simultaneously, as described in the '998 Patent. The approach described herein, which includes expanding the tissue and then supporting the expanded tissue, may be used to treat these same conditions. Such procedures may be performed percutaneously through a cannula or other minimally invasive instrument or in an open procedure.

Figure 17:
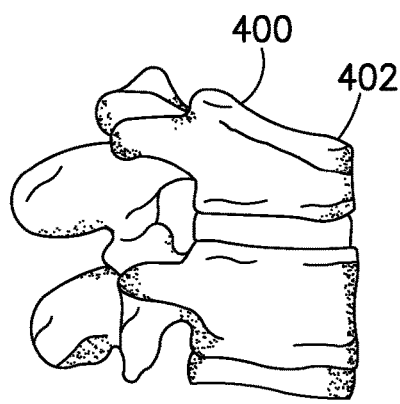
FIG. 17 shows a vertebral body having a compression fracture displacing its superior and anterior edge.
Figure 18:
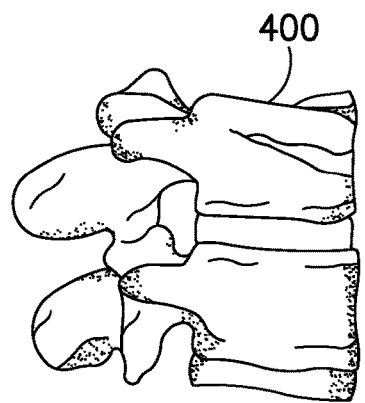
FIG. 18 shows a vertebral body, following treatment of a compression fracture.
Figure 19:
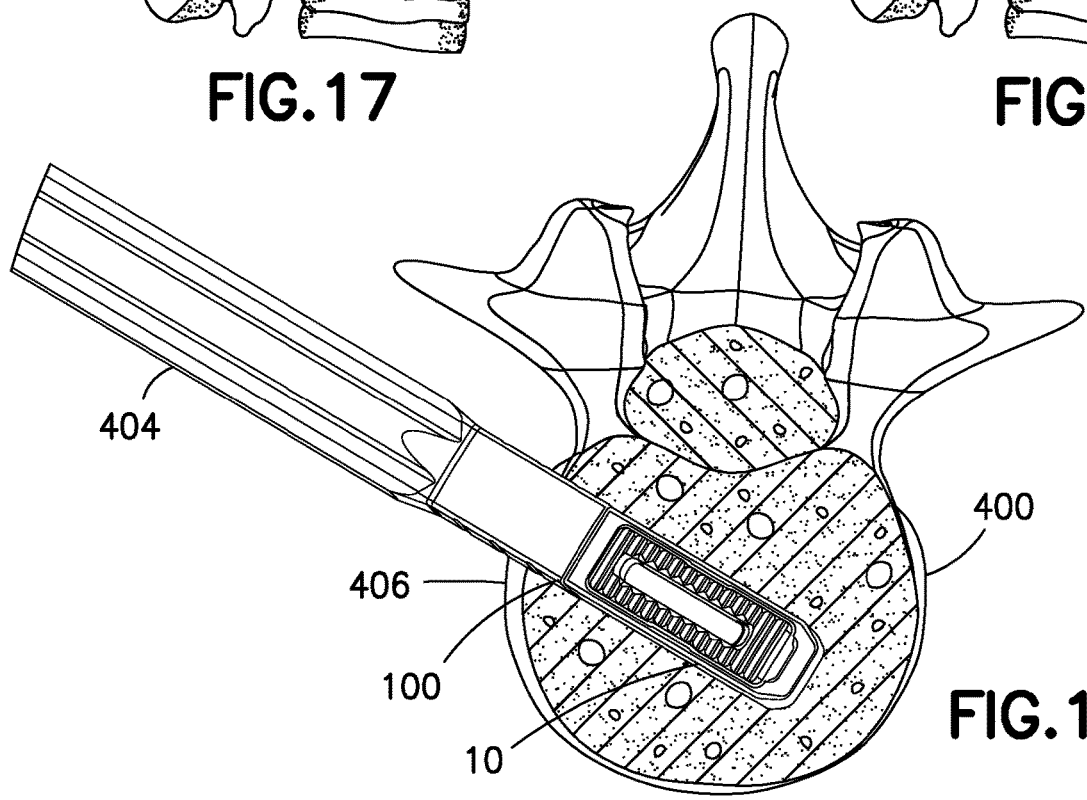
FIG. 19 illustrates a plan view of an insertion apparatus according to another embodiment of the invention, placed within a vertebral body of FIG. 17, shown in cross-section.

The expansion device is now described in this section by its application as a spinal implant to vertebral compression fractures. FIG. 17 shows a vertebral body 400 having a compression fracture displacing its superior and anterior edge 402. FIG. 18 shows vertebral body 400 wherein the height has been restored. FIG. 19 illustrates an extrapedicular approach to vertebral body 400 wherein an access cannula 404 is placed through the posterolateral wall 406 of vertebral body 400. Other approaches may optionally be used for placing a cannula into a vertebral body such as a transpedicular approach to the vertebral body wherein an access cannula may be placed through the pedicle. In the extrapedicular approach, two cannulae 404 may be placed bilaterally, one on each side.

Figure 20:
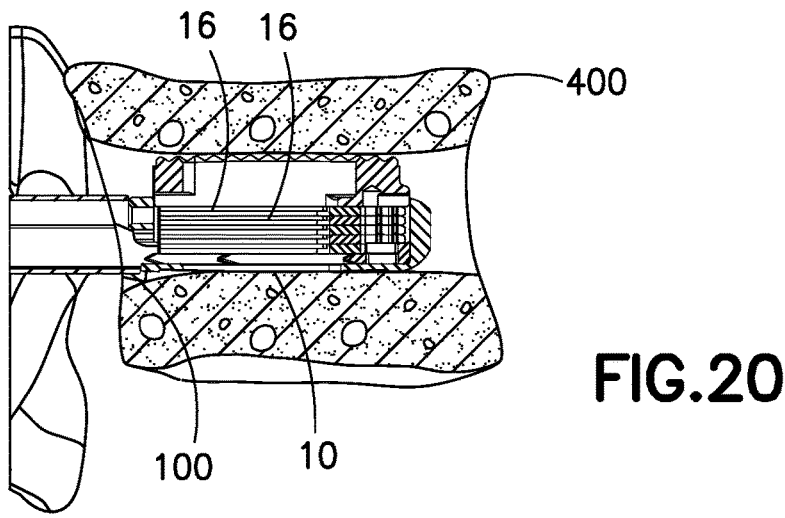
FIG. 20 shows a side view of the insertion apparatus of FIG. 19 being deployed within a vertebral body, shown in sectional view.

The procedure for the placement of access cannula 404 into verterbral body 400 is more fully described in the '998 Patent, incorporated herein by reference. Cannula 404 in this particular arrangement is preferably rectangular in cross-section, although cannulae of other cross-sections, such as circular may be used. Further, cannula 404 may be of fixed configuration or expandable. Once access cannula 404 is in place, an expandable device 10 supported by inserter 100 may be introduced into vertebral body 400 through cannula 404. This application of the invention contemplates expanding expandable device 10 by the inserter 100 from an unexpanded condition as shown, for example in FIG. 1*b* to the expanded height as shown in FIG. 20 to ultimately reduce the vertebral compression fracture and substantially restore the normal anatomic height of vertebral body 400, inserting one or more inserts, such as inserts 16, as described herein, to form a stack of inserts 16 between the expanded superior endplate 12 and inferior endplate 14 of expandable device 10. In the particular arrangement being described for vertebral compression fracture reduction, expandable device 10 may have a length of approximately 25 mm, a width of approximately 10 mm, and an unexpanded height H of approximately 7 mm. The height H may be expanded by 5 mm and supported by the introduction of five inserts 16, as shown in FIG. 20, each insert 16 as described herein having a thickness of 1 mm. It should be appreciated that the height H may be increased by other amounts and more or less than five inserts used, and that device 10 may be configured in other dimensions as set forth in the '998 Patent.

When the fracture is reduced as depicted in FIG. 18, or when the physician determines that an adequate number of inserts 16 has been inserted, the inserter 100 may be separated from device 10 and removed from cannula 404 while expanded device 10 remains within vertebral body 400. Access cannula 404 is left in place. Suitable bone filler may be injected into vertebral body 400 through cannula 404 to encapsulate device 10, provide weight bearing structure and increase stability of vertebral body 400. Bone filler may flow through device 10 and the insert column and out to the surrounding bone to interdigitate with cancellous bone.

It should therefore be understood that while various embodiments of the invention have been presented herein, various changes, modifications and further applications may be made without departing from the spirit of the invention and the scope of the appended claims.

What is claimed is:

1. An inserter for inserting an interbody fusion device into an intradiscal space between two opposing vertebral bodies, comprising:
   a frame having an opening therethrough;
   an elongate guide pin having a distal end and a proximal end, said guide pin being slidable within said frame opening and detachably supported by said frame, said distal end of said guide pin including an engagement portion for releasable engagement with said interbody fusion device, said proximal end of said guide pin including a rotatable member configured to engage said frame and releasably connect said frame to said interbody fusion device, said guide pin being configured to serve as a locator for subsequent attachment to another apparatus, including an apparatus for introducing bone graft material into said interbody fusion device, and
   a pair of hand grips, one of which is fixedly secured to said frame and the other of which is pivotally connected to said frame.

2. The inserter of claim 1 wherein said engagement portion of said guide pin is threaded.

3. The inserter of claim 2, wherein said rotatable member is a knob threadably attached to the proximal end of said guide pin.

4. The inserter of claim 3, further including an elongate cover having a distal end and a proximal end and supported by said frame, said opening extending lengthwise through the cover.

5. The inserter of claim 4, wherein said cover includes at least one tab projecting outwardly from the distal end of said cover and configured for engagement with said interbody fusion device to assist in rigidly securing said inserter to said interbody fusion device.

6. The inserter of claim 5, wherein said cover comprises two tabs projecting from the distal end thereof and spaced apart from each other.

7. The inserter of claim 1, wherein said inserter further comprises a graft shield projecting from the distal end of said inserter and being of size and configuration to extend into said interbody fusion device.

8. An inserter for inserting an interbody fusion device into an intradiscal space between two opposing vertebral bodies, comprising:
   a distal end and a proximal end, said distal end being releasably attachable to said interbody fusion device, said inserter including an actuator at said proximal end and an expansion component at said distal end operably coupled to said actuator to cooperatively engage expansion structure in said interbody fusion device for expanding said device, said inserter including an elongate guide pin having a distal end and a proximal end, said guide pin being slidable within and detachably supported by said inserter, said distal end of said guide pin including an engagement portion for releasable engagement with said interbody fusion device, said proximal end of said guide pin including a rotatable member configured to engage said inserter and releasably connect said inserter to said interbody fusion device, said guide pin being configured to serve as a locator for subsequent attachment to another apparatus, including an apparatus for introducing bone graft material into said interbody fusion device.

9. The inserter of claim 8, further including at least one insert movably supported by said inserter for slidable insertion into said device, said inserter including a driver operably coupled to said actuator for contacting and driving said at least one insert into said device.

10. The inserter of claim 8, further including a flexible graft shield supported at one end in a cantilevered manner by said inserter with an opposite end being unsupported and free to flex.

11. The inserter of claim 10, wherein said graft shield is elongate and generally flat.

12. The inserter of claim 8, wherein engagement portion of guide pin is threaded for releasable threaded engagement into said device.

13. The inserter of claim 12, wherein said rotatable member is a threaded knob for compressing and releasably attaching said inserter to said interbody fusion device.

14. The inserter of claim 8, further including an elongate track having a distal end and a proximal end, said engagement portion of said guide pin projecting from the distal end of said track.

15. The inserter of claim 14, wherein said track is configured to linearly support a plurality of inserts for sequential individual insertion into said interbody fusion device.

16. The inserter of claim 8, further comprising a frame, said frame supporting said actuator.

17. The inserter of claim 16, further comprising a pair of hand grips, one of which is fixedly secured to said frame and the other of which is pivotally connected to said frame.

* * * * *